(12) United States Patent
Aoki et al.

(10) Patent No.: US 7,789,511 B2
(45) Date of Patent: Sep. 7, 2010

(54) EYE MOVEMENT MEASURING APPARATUS, EYE MOVEMENT MEASURING METHOD AND RECORDING MEDIUM

(75) Inventors: Hiroyuki Aoki, Tokyo (JP); Takashi Fujimura, Tokyo (JP); Hisashi Tsukada, Tokyo (JP); Tsutomu Kikawa, Tokyo (JP); Yasufumi Fukuma, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 240 days.

(21) Appl. No.: 11/845,358

(22) Filed: Aug. 27, 2007

(65) Prior Publication Data

US 2008/0259275 A1  Oct. 23, 2008

(30) Foreign Application Priority Data

Aug. 29, 2006 (JP) ............................... 2006-232739

(51) Int. Cl.
*A61B 3/113* (2006.01)
(52) U.S. Cl. ........................................ 351/205; 351/209
(58) Field of Classification Search ................. 351/205, 351/206, 200, 212, 214, 221
See application file for complete search history.

(56) References Cited

U.S. PATENT DOCUMENTS

| 5,537,162 A | 7/1996 | Hellmuth et al. |
|---|---|---|
| 2006/0114411 A1 | 6/2006 | Wei et al. |
| 2006/0164653 A1 | 7/2006 | Everett et al. |
| 2009/0141240 A1* | 6/2009 | Weitz et al. ................. 351/246 |

FOREIGN PATENT DOCUMENTS

| JP | 2005-066358 | 3/2005 |
|---|---|---|
| JP | 2005-205024 | 8/2005 |
| JP | 2005-211329 | 8/2005 |
| JP | 2005-323905 | 11/2005 |

OTHER PUBLICATIONS

Petrig, B.L.; Gigun, J.; Curchod, M.G.: Motion Estimation of Ocular Fundus Images Image Processing, 1996. Proceedings., International Conference on Publication Date: Sep. 16-19, 1996; vol. 3, p. 691-694; Lausanne, Switzerland.
Hideo Kawai, Shinichi Tamura, Kazutaka Kani, Komyo Kariya: Eye Movement Analysis System Using Fundus Images Pattern Recognition 19(1): 77-84 (1986), Elmsford, NY.
Ott D. and Daunicht, W.J.: Eye Movement Measurement iwth the Scanning Laser Ophthalmoscope Clinical vision sciences (Clin. vis. sci.) ISSN 0887-6169 Coden CVSCE; 1992, vol. 7, No. 6 (27 ref.), pp. 551-556.
Lakmann, Raimund: Efficient detection of eye movements in video image sequences Visual communications and image processing. Conference, Perth, Australie (Jun. 20, 2000) 2000, vol. 4067 (3), pp. 106-113; Pergamon Press, Oxford, ETATS-UNIS (1986-1993) (Revue).
European Search Report dated Jan. 10, 2008, issued in European Patent Application No. 07 01 6193.
Chinese Office Action dated Jan. 29, 2010, issued in Chinese Patent Application No. 2007101455184.

* cited by examiner

*Primary Examiner*—Scott J Sugarman
*Assistant Examiner*—Tuyen Q Tra
(74) *Attorney, Agent, or Firm*—Edwards Angell Palmer & Dodge LLP

(57) ABSTRACT

An eye movement measuring apparatus comprises: an image forming part configured to obtain data optically to form a fundus oculi image of an eye based on the obtained data; and an image analysis part configured to analyze the formed fundus oculi image to determine eye movement of the eye.

7 Claims, 16 Drawing Sheets

EYE MOVEMENT MEASURING APPARATUS, EYE MOVEMENT MEASURING METHOD AND RECORDING MEDIUM

BACKGROUND OF THE INVENTION

1. Field of the Invention

The present invention relates to an eye movement measuring apparatus for measuring eye movement of an eye, an eye movement measuring method, and an recording medium. In specific, the present invention relates to a technique for measuring eye movement based on a fundus oculi image.

2. Description of the Related Art

Conventional techniques for measuring eye movement are disclosed in JP Patent laid-open No. 2005-66358, JP Patent laid-open No. 2005-205024, JP Patent laid-open No. 2005-211329, and JP Patent laid-open No. 2005-323905. The technique disclosed in JP Patent laid-open No. 2005-66358 is to determine the center, radius and a plurality of characteristic regions of an eye based on a moving image of eye movement having been imaged and detecting movement of the eye based on the determination, thereby facilitating the setting of an index for analyzing eye movement.

The technique disclosed in JP Patent laid-open No. 2005-205024 is to irradiate the eyelid of an eye with near-infrared light and measure eye movement based on the intensity of reflection light, thereby improving the sensitivity of measurement of eye movement in a state where the eye is closed.

The technique disclosed in JP Patent laid-open No. 2005-211329 is to improve measurement accuracy, by irradiating the corneal of an eye with light, detecting an image of reflection light of the corneal with a light-detecting part including a plurality of pixels arranged two-dimensionally to generate imaging data showing the amount of incident light for every pixel, and setting the resolution and imaging region in the light-detecting part based on information on movement of a position for the corneal reflection light image to enter the light-detecting part.

In the technique disclosed in JP Patent laid-open No. 2005-323905, a first imaging device for wide-angle imaging of a subject and a second imaging device for imaging the eye of the subject are provided. This technique is to improve measurement accuracy by: calculating control information for controlling the direction of the second imaging device from a picture imaged by the first imaging device; generating a control signal for controlling the direction of the second imaging device by tracing the position of the eye from a picture imaged by the second imaging device; calculating location information of the eye gaze from the picture imaged by the second imaging device; checking a tracing state of the eye in calculation of the location information of the eye gaze; and controlling the direction of the second imaging device by any one of the above control signals based on the results of checking.

As described above, a variety of techniques for measuring eye movement have been developed. In particular, an effort has been put into improvement of measurement accuracy. However, since the amount of movement of an eye during eye movement is extremely small and the moving time is short, it is desired to further improve the measurement accuracy.

SUMMARY OF THE INVENTION

In a first aspect of the present invention, an eye movement measuring apparatus comprises: an image forming part configured to obtain data optically to form a fundus oculi image of an eye based on the obtained data; and an image analysis part configured to analyze the formed fundus oculi image to determine eye movement of the eye.

Further, in a second aspect of the present invention, an eye movement measuring method comprises the steps of: obtaining data optically to form a fundus oculi image of an eye based on the obtained data; and analyzing the formed fundus oculi image to determine eye movement of the eye.

Furthermore, in a third aspect of the present invention, a computer-readable recording medium having a computer-readable code to cause a computer to execute processing is characterized in that: the computer has an image storage configured to store a fundus oculi image of an eye; and the processing includes the process of analyzing the stored fundus oculi image to determine eye movement of the eye.

According to the present embodiment, the eye movement measuring apparatus is configured to analyze a fundus oculi image of an eye to determine eye movement of the eye. Typically, high accuracy is necessary for capturing a fundus oculi image of an eye. Therefore, compared with measurement of eye movement based on an image imaged by a television camera or a corneal reflection light image as conventional, it is possible to measure eye movement with higher accuracy.

DETAILED DESCRIPTION OF THE PREFERRED EMBODIMENT

A preferred embodiment of an eye movement measuring apparatus, an eye movement measuring method, and an recording medium according to the present invention will be described in detail referring to the accompanying drawings.

The present invention is for measuring extremely minute eye movement with high accuracy by analyzing the fundus oculi image of an eye. In the present invention, the term "eye movement" includes not only movement of an eye caused by the ocular muscle, such as small involuntary eye movement, pursuit movement and saccade movement of an eye, but also movement of an eye caused by any factor other than the ocular muscle, such as movement of the eye position due to pulsation.

Eye Movement Measuring Apparatus

First, an example of the configuration of the eye movement measuring apparatus according to the present embodiment will be described referring to FIGS. 1 to 12.

Figure 1:
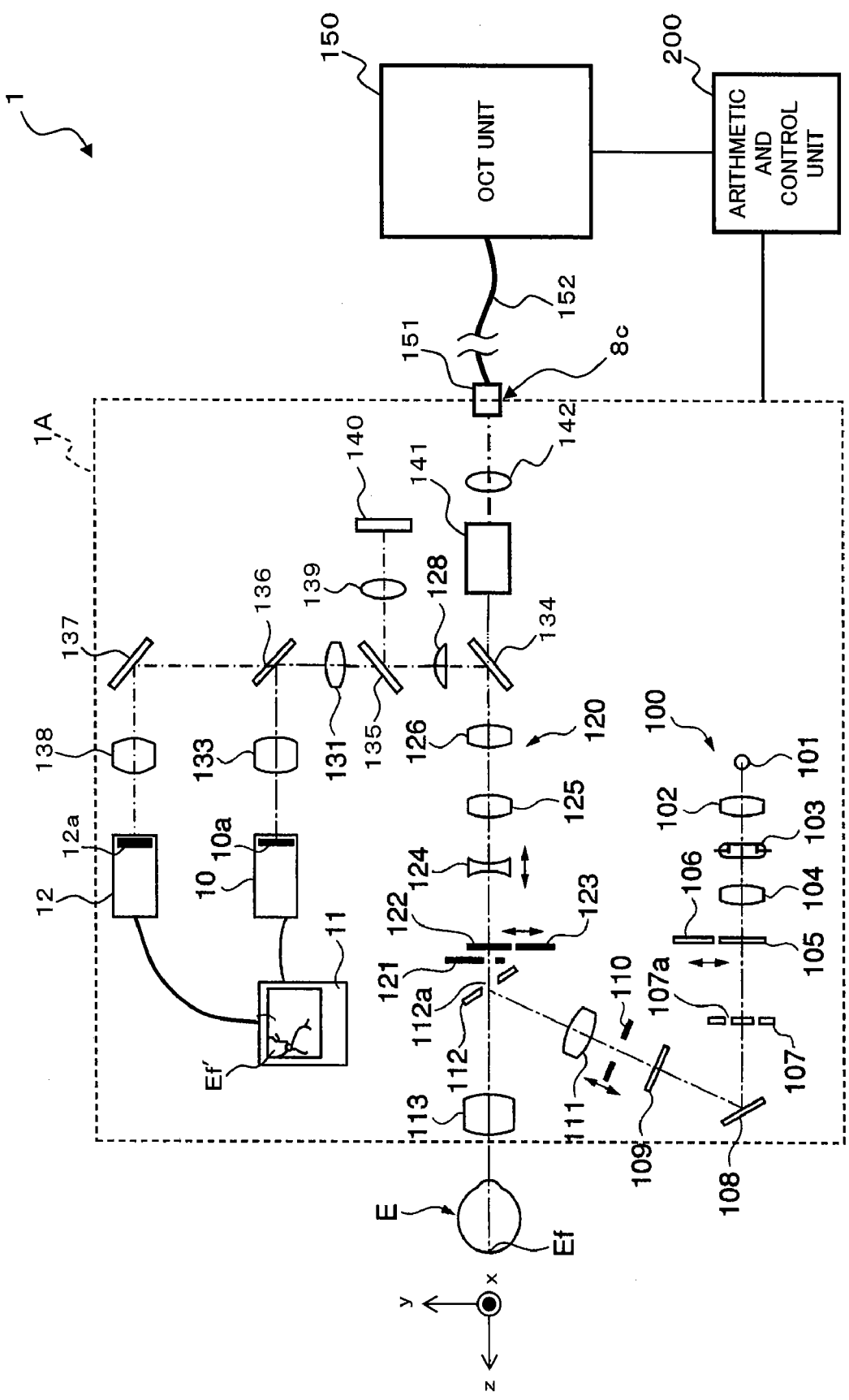
FIG. 1 is a schematic diagram showing an entire configuration of an eye movement measuring apparatus according to a preferred embodiment of the present invention.
Figure 2:
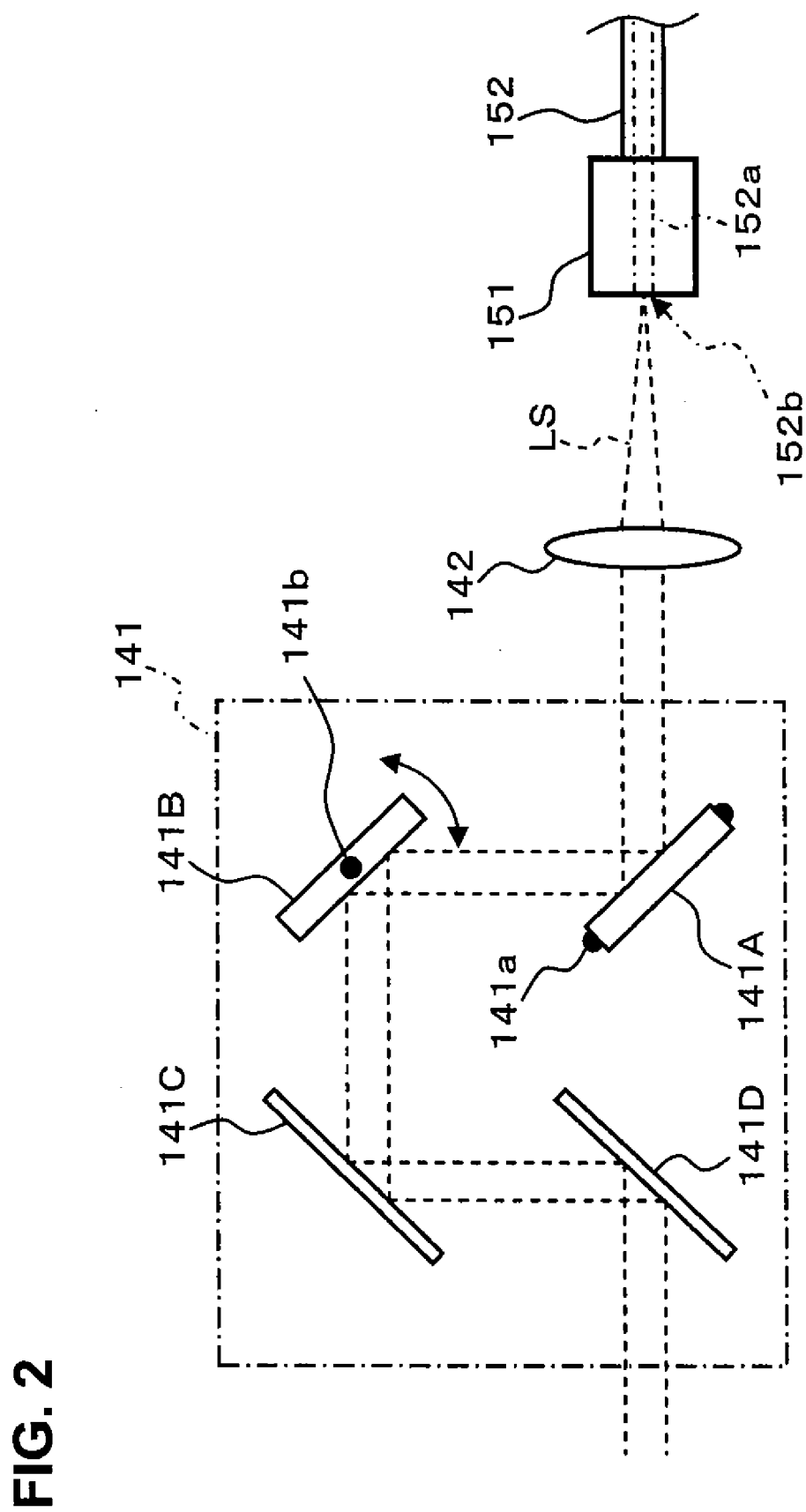
FIG. 2 is a schematic diagram showing a configuration of an optical system of the eye movement measuring apparatus according to the preferred embodiment of the present invention.
Figure 3:
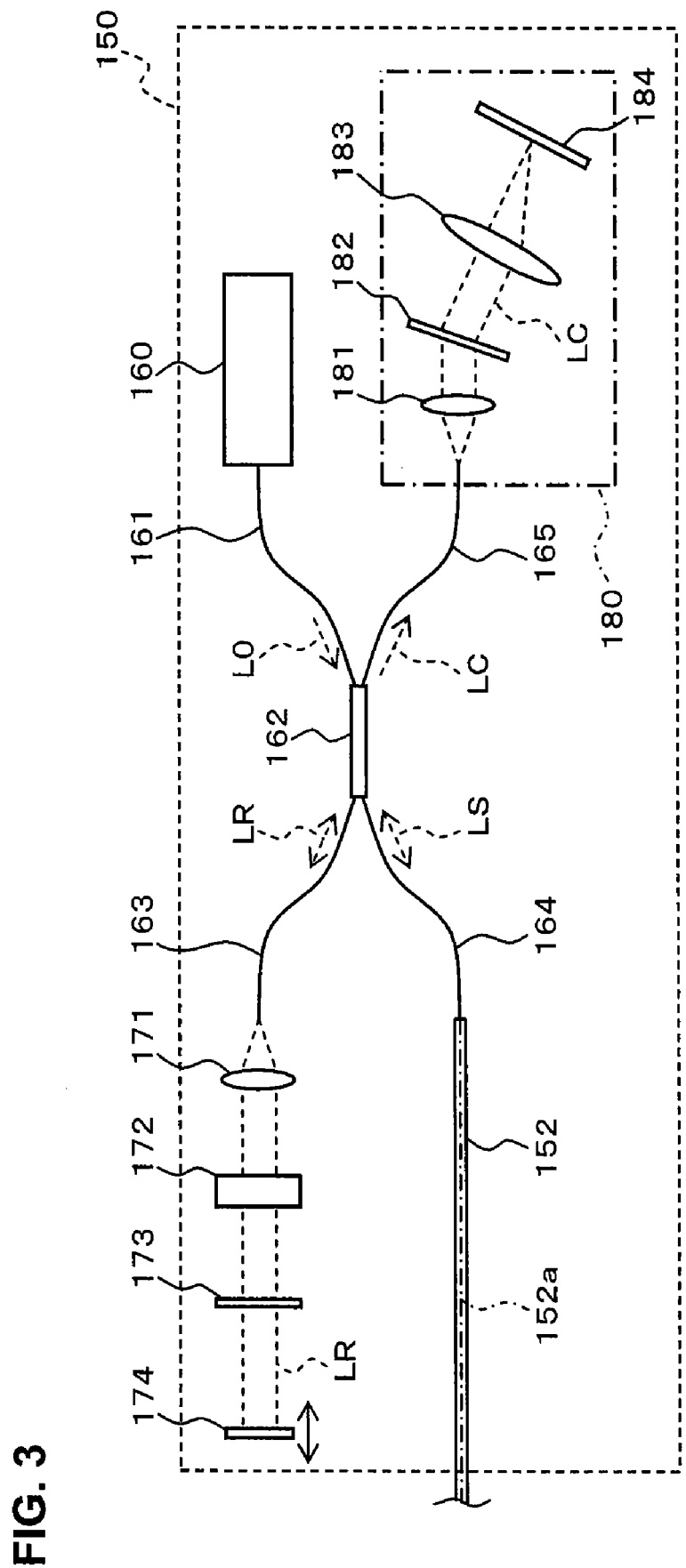
FIG. 3 is a schematic diagram showing a configuration of the eye movement measuring apparatus according to the preferred embodiment of the present invention.
Figure 4:
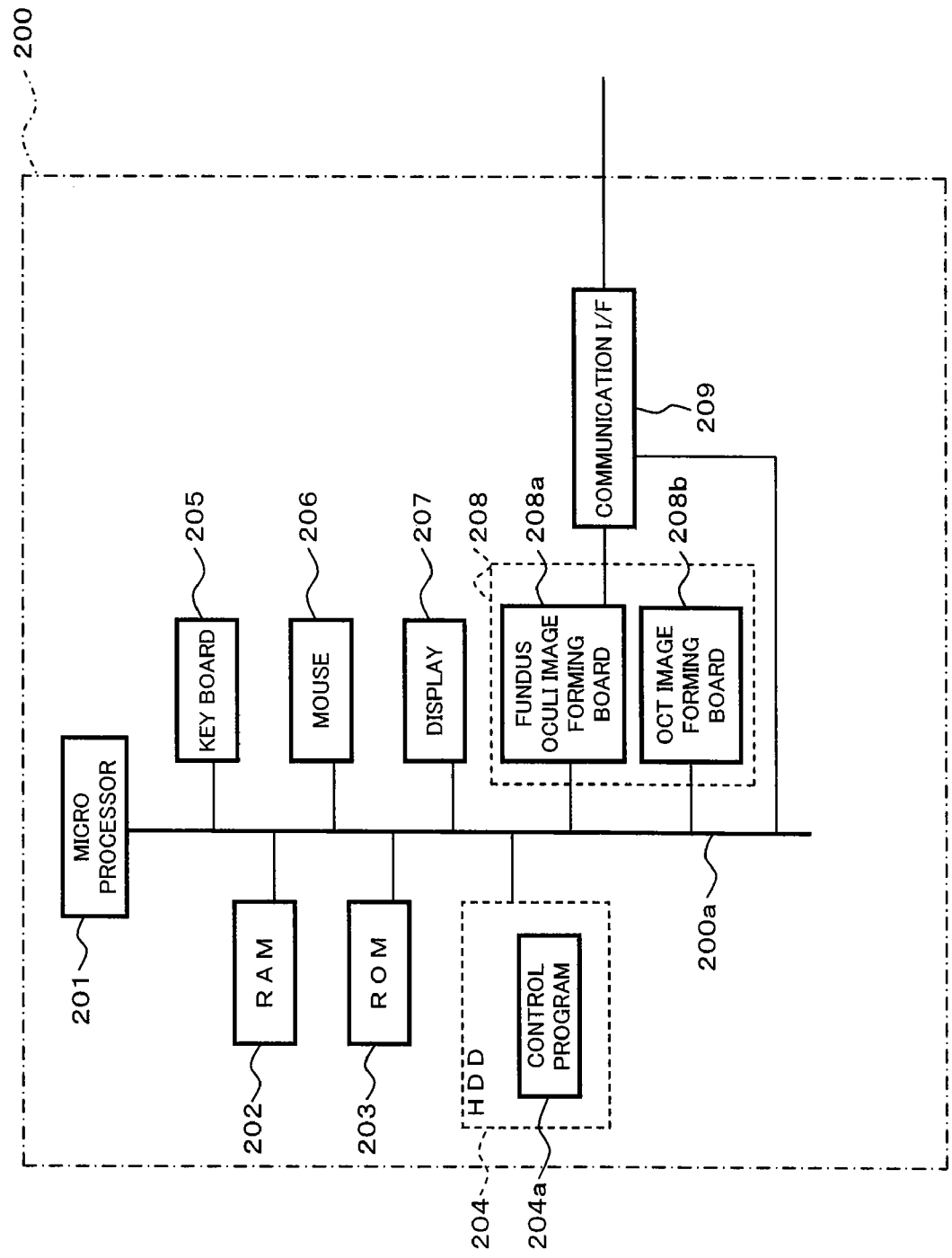
FIG. 4 is a schematic block diagram showing a hardware configuration of an arithmetic and control unit of the eye movement measuring apparatus according to the preferred embodiment of the present invention.
Figure 5:
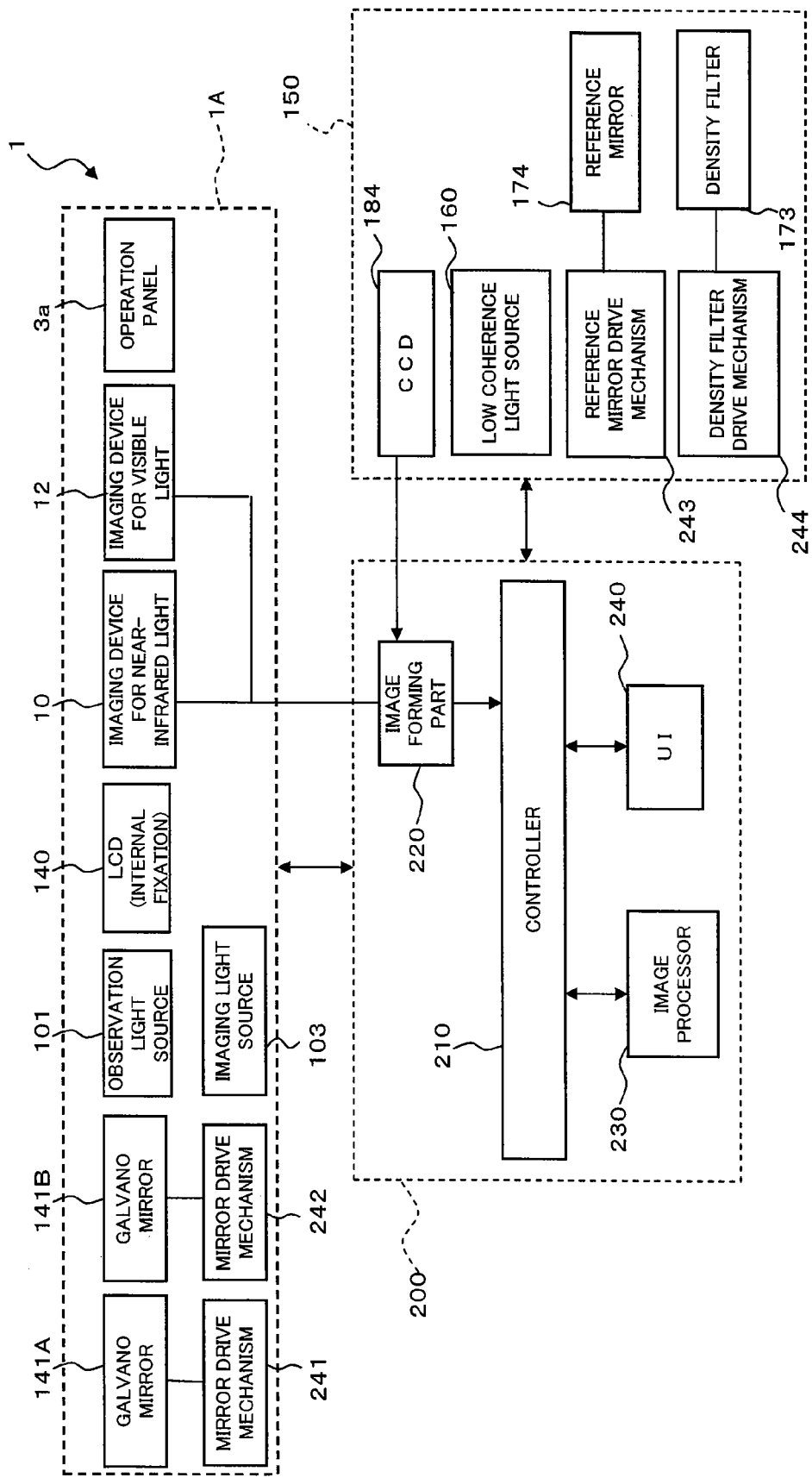
FIG. 5 is a schematic block diagram showing a configuration of a control system of the eye movement measuring apparatus according to the preferred embodiment of the present invention.
Figure 6:
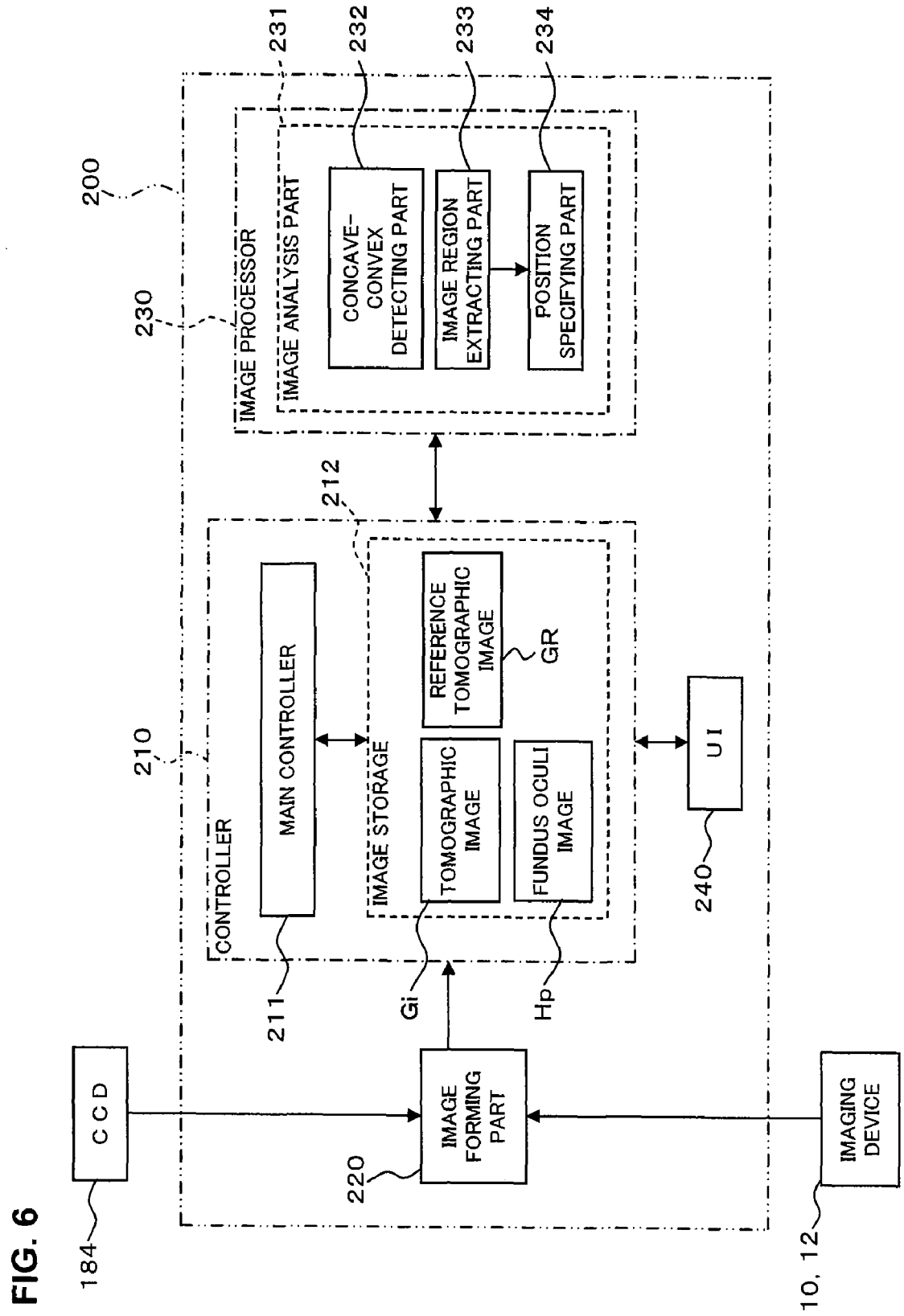
FIG. 6 is a schematic block diagram showing a configuration of a control system of the arithmetic and control unit of the eye movement measuring apparatus according to the preferred embodiment of the present invention.
Figure 7:
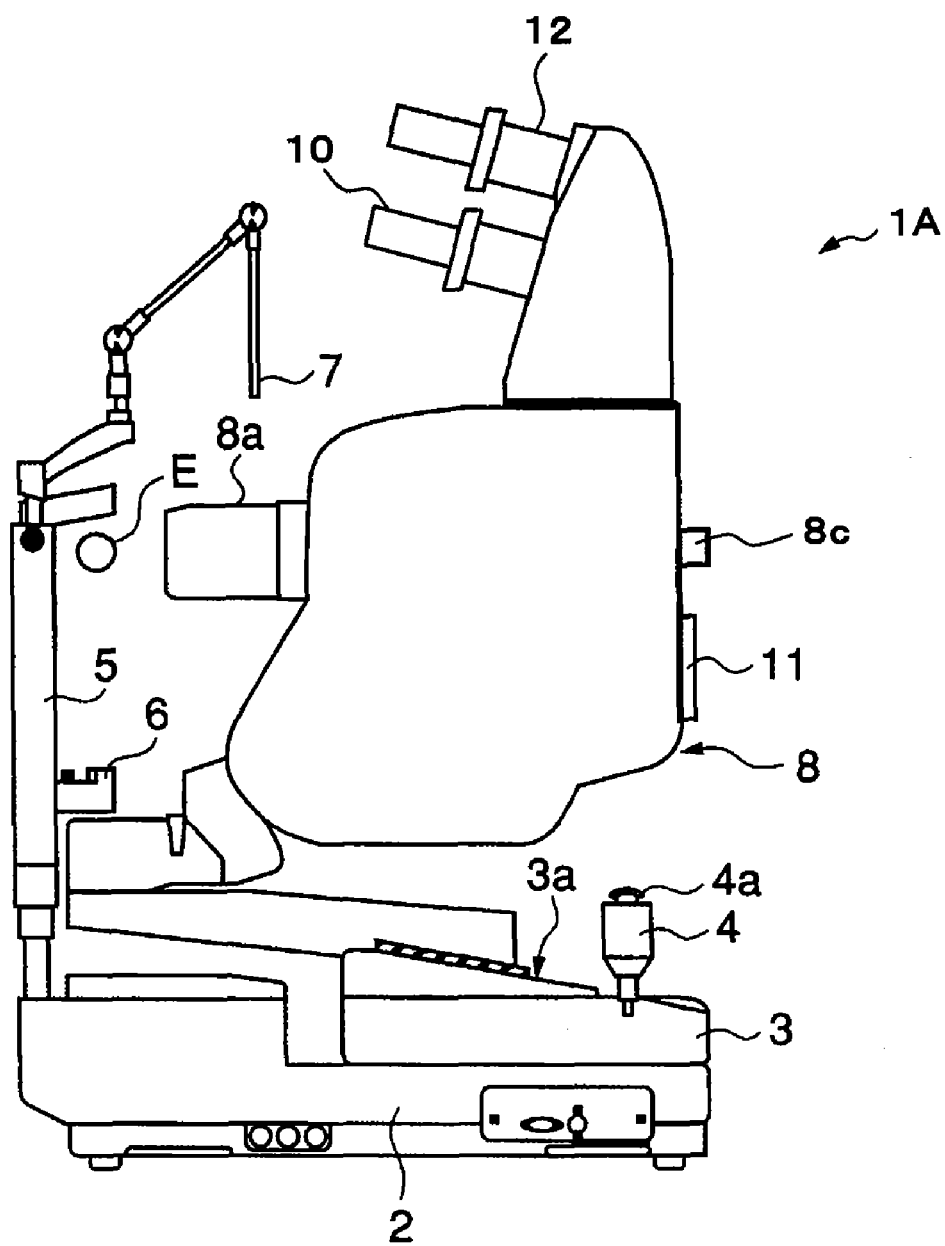
FIG. 7 is a schematic side view showing a appearance of a retinal camera unit of the eye movement measuring apparatus according to the preferred embodiment of the present invention.
Figure 8:
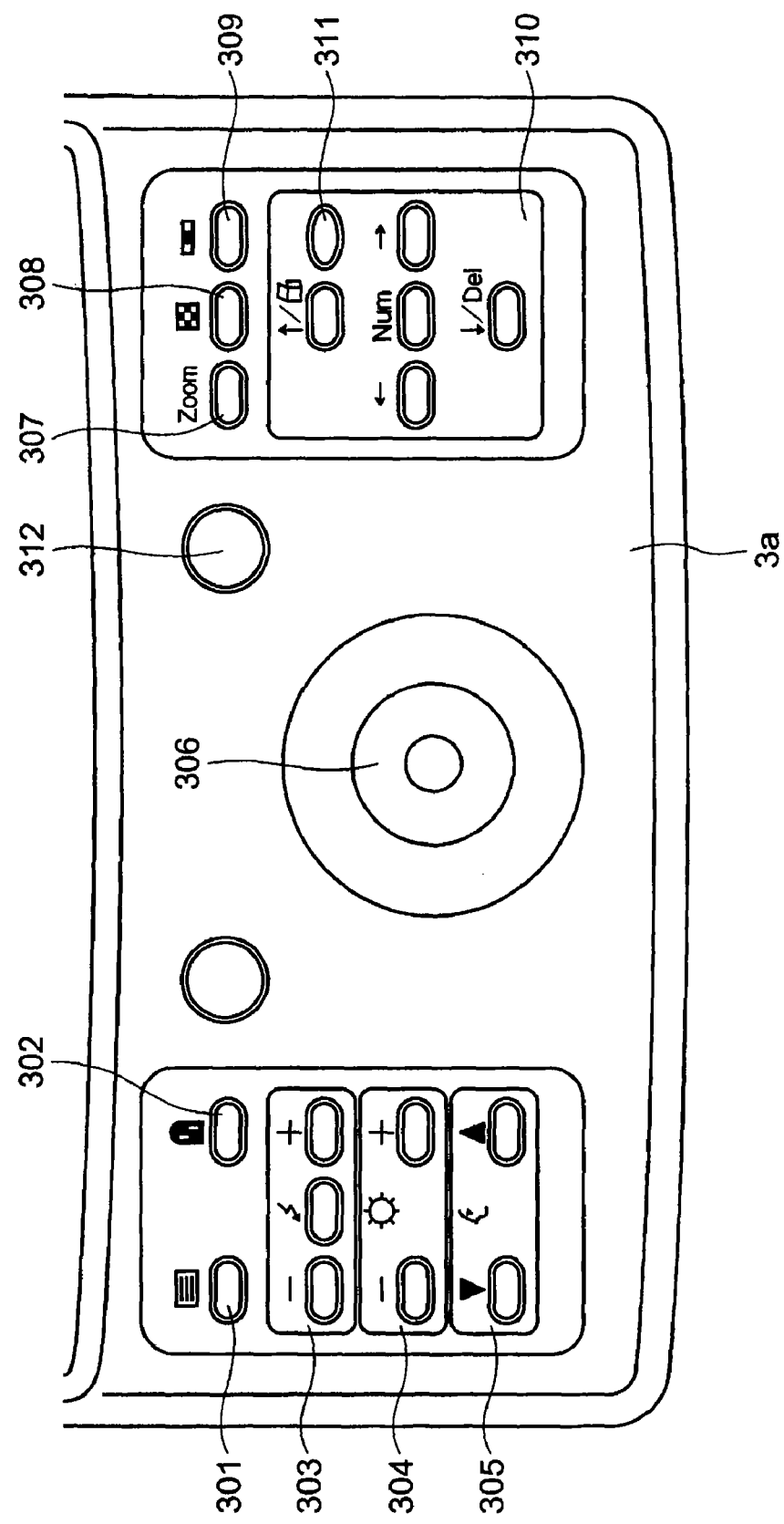
FIG. 8 is a schematic diagram showing an appearance of an operation panel of the retinal camera unit according to the preferred embodiment of the present invention.
Figure 10:
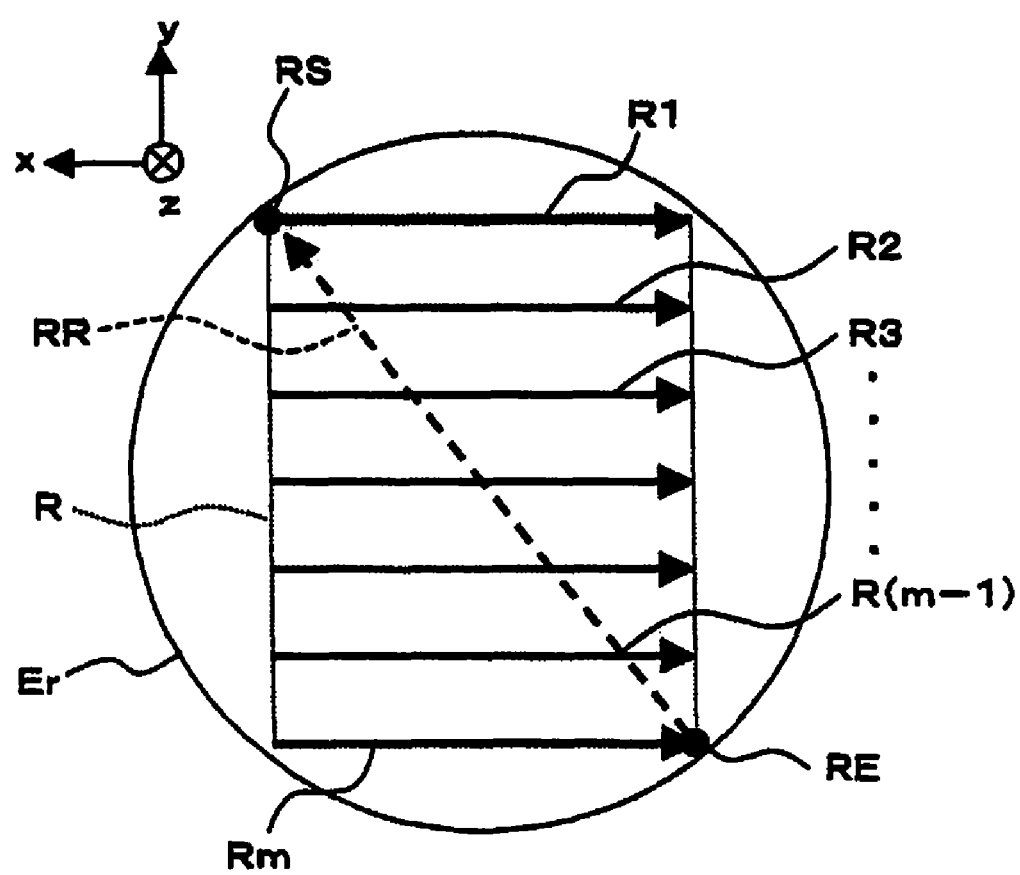
FIG. 10 is a schematic explanation view for explaining scanning of signal light of the eye movement measuring apparatus according to the preferred embodiment of the eye movement measuring apparatus of the present invention.
Figure 11:
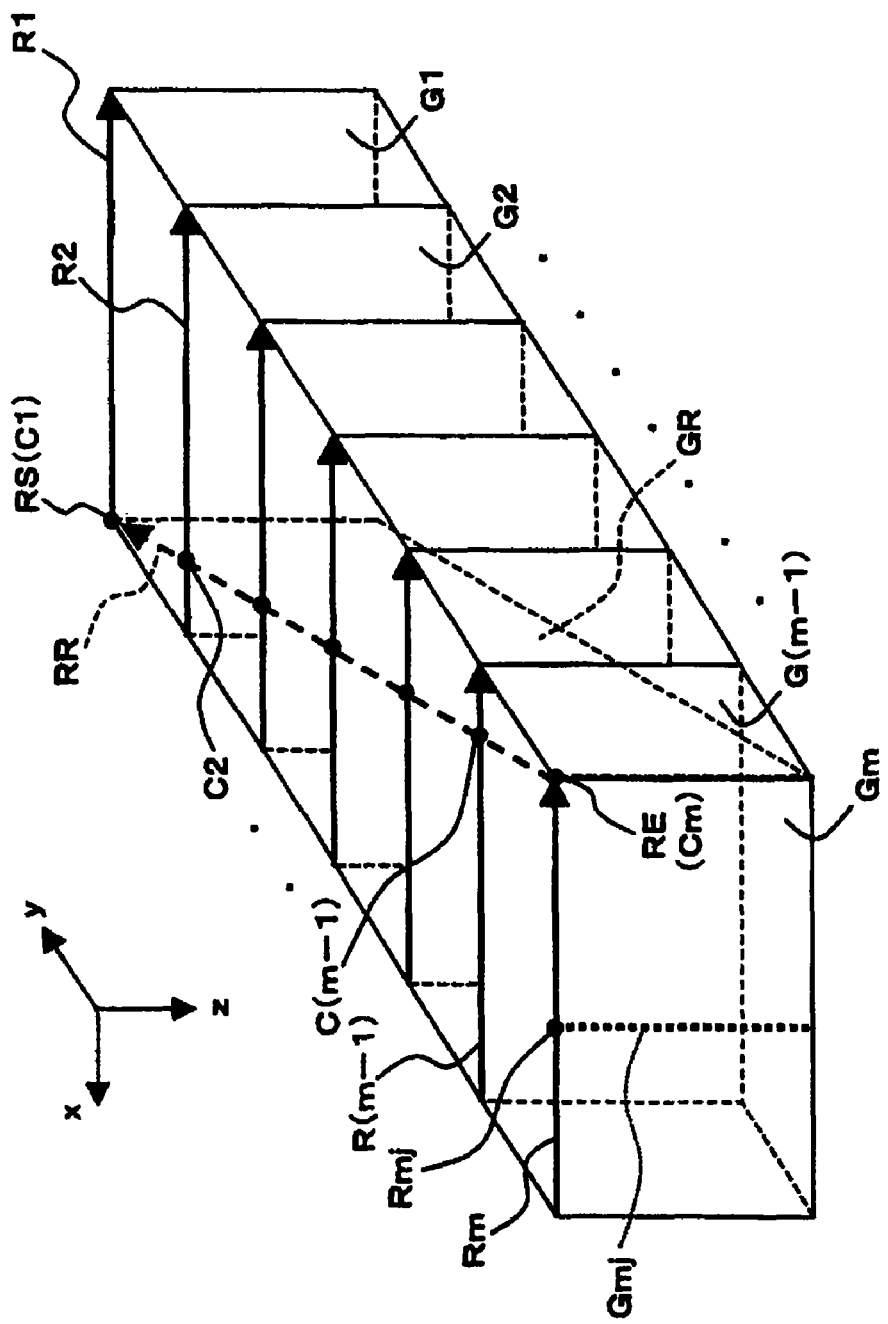
FIG. 11 is a schematic explanation view showing scanning of signal light and formation of a tomographic image of the eye movement measuring apparatus according to the preferred embodiment of the present invention.
Figure 12:
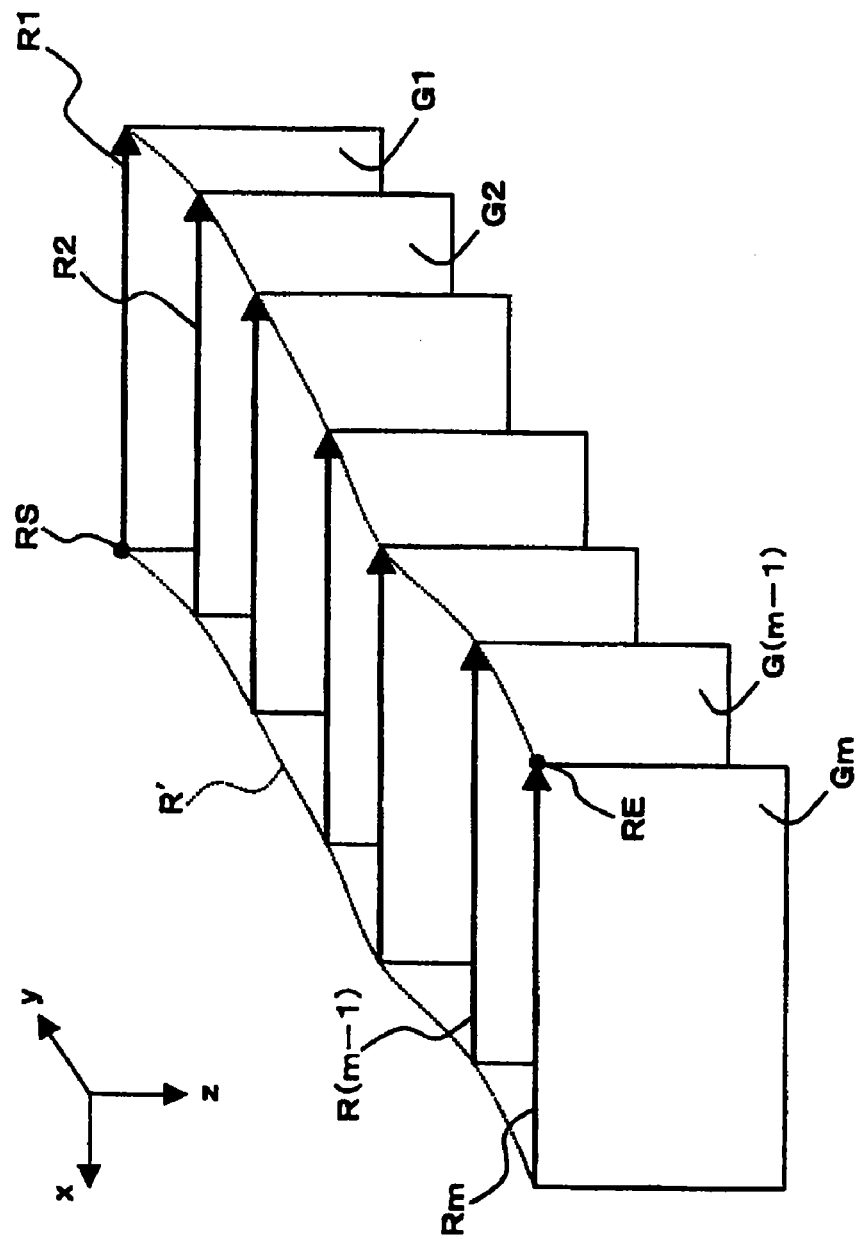
FIG. 12 is a schematic explanation view showing formation of a tomographic image in a case where eye movement of an eye occurs during scanning of signal light of the eye movement measuring apparatus according to the preferred embodiment of the present invention.

FIG. 1 represents the overall configuration of an eye movement measuring apparatus 1 and the configuration of a retinal camera unit 1A according to the present embodiment. FIG. 2 represents the configuration of a scanning unit 141 of the retinal camera unit 1A. FIG. 3 represents the configuration of an OCT unit 150. FIG. 4 represents the configuration of an arithmetic and control unit 200. FIGS. 5 and 6 represent overviews of the control system configuration of the eye movement measuring apparatus 1. FIG. 7 represents the appearance of the retinal camera unit 1A. FIG. 8 represents the appearance of an operation panel 3a of the retinal camera unit 1A. FIGS. 9 and 10 represent modes of scanning a signal light for capturing a tomographic image of a fundus oculi. FIGS. 11 and 12 represent modes of a process of forming a tomographic image.

Overall Configuration

The eye movement measuring apparatus 1 according to the present embodiment comprises, as shown in FIG. 1, the retinal camera unit 1A that images a fundus oculi image, the OCT unit 150 that stores the optical system of an optical image measuring apparatus (optical coherence tomography apparatus; OCT apparatus) capturing a tomographic image of a fundus oculi, and the arithmetic and control unit 200 that executes a variety of arithmetic processes and control processes.

To the OCT unit 150, one end of a connection line 152 is connected. To the other end of the connection line 152, a connector 151 is attached. This connector 151 is mounted on a mounting part 8c (described later) of the retinal camera unit 1A shown in FIG. 7. Further, a conductive optical fiber runs through the inside of the connection line 152. Thus, the OCT unit 150 and the retinal camera unit 1A are optically connected via the connection line 152.

Configuration of Retinal Camera Unit

The retinal camera unit 1A is a device configured to form a two-dimensional image of the surface of a fundus oculi of an eye based on optically obtained data (data detected by imaging devices 10 and 12).

First, referring to FIG. 7, the appearance of the retinal camera unit 1A will be described. This retinal camera unit 1A is provided with a platform 3 mounted on a base 2 so as to be slidable in the front and rear, right and left directions (horizontal direction). On this platform 3, an operation panel 3a and control lever 4 for an examiner to conduct various operations are installed.

The examiner can three-dimensionally move the platform 3 on the base 2 by operating the control lever 4. On the top of the control lever 4, an operation button 4a pushed down at the time of instruction of capture of a fundus oculi image is installed. The configuration of the operation panel 3a will be described later.

On the base 2, a post 5 is installed standing upright. The post 5 is provided with a jaw holder 6 on which the jaw of a patient is rested, and an external fixation lamp 7 that emits light for fixing an eye E.

On the platform 3, a main body part 8 is installed to accommodate various optical systems and control systems of the retinal camera unit 1A. On the eye E side of the main body part 8 (on the left side of the sheet of FIG. 7), an objective lens part 8a disposed so as to face the eye E is installed.

Further, the main body part 8 is provided with the imaging devices 10 and 12, such as a television camera for imaging a still image and a moving image of a fundus oculi of the eye E. The imaging device 10 detects light having a wavelength of a near-infrared region. The imaging device 12 detects light having a wavelength of a visible region. The imaging devices 10 and 12 are attachable to and detachable from the main body part 8, respectively. Although two imaging devices are mounted on the retinal camera unit 1A in the present embodiment, the number of the mounted devices is arbitrary.

Furthermore, on the examiner's side of the main body part 8, a touch panel monitor 11 is installed. On this touch panel monitor 11, fundus oculi images of the eye E formed based on video signals output from the imaging devices 10 and 12 are displayed. Moreover, on the touch panel monitor 11, a two-dimensional coordinate system taking the center of the screen as the origin is displayed overlapped with a fundus oculi image. When the examiner touches a desired position on the screen, the coordinate value corresponding to the touched position is displayed.

The retinal camera unit 1A is provided with an illumination optical system 100 illuminating a fundus oculi Ef of the eye E, and an imaging optical system 120 guiding the fundus reflection light of the illumination light to the imaging device 10.

Next, the configuration of the optical system of the retinal camera unit 1A will be described referring to FIGS. 1 and 2. The optical system of the retinal camera unit 1A comprises the illuminating optical system 100 and the imaging optical system 120. The optical system of the retinal camera unit 1A is aligned with the fundus oculi Ef before the fundus oculi Ef is imaged (that is, the main body part 8 is moved in the x direction, y direction and z direction shown in FIG. 1 to arrange the optical system into a suitable position for imaging).

The illumination optical system 100 irradiates the eye E with an illumination light for imaging an image of the fundus oculi Ef. The imaging optical system 120 receives reflection light from the fundus oculi of the illumination light, from the illuminating optical system 100, and images an image of the fundus oculi Ef. Moreover, the imaging optical system 120 functions so as to guide signal light from the OCT unit 150 to the fundus oculi Ef and guide the signal light returning from the fundus oculi Ef to the OCT unit 150.

The illumination optical system 100 comprises: an observation light source 101; a condenser lens 102; an imaging light source 103; a condenser lens 104; exciter filters 105 and 106; a ring light-transmitting plate 107; a mirror 108; an LCD (liquid crystal display) 109; an illumination diaphragm 110; a relay lens 111; an aperture mirror 112; and an objective lens 113.

The observation light source 101 outputs illumination light (observation illumination light) having a wavelength of a visible region in the range of, for example, about 400 to 700 nm, and is composed of, for example, a halogen lamp. The condenser lens 102 is an optical element for almost evenly illuminating observation illumination light on the fundus oculi Ef by condensing the observation illumination light emitted from the observation light source 101.

The imaging light source 103 outputs illumination light (imaging illumination light) having a wavelength of a near-infrared region in the range of, for example, about 700 to 800 nm, and is composed of, for example, a xenon lamp. The near-infrared light output from the imaging light source 103 is set so as to have a shorter wavelength than light used in the OCT unit 150 (described later). The imaging light source 103 emits flashlight when the fundus oculi Ef is imaged. The condenser lens 104 is an optical element for almost evenly irradiating the fundus oculi Ef with imaging illumination light by condensing the imaging illumination light emitted from the imaging light source 103.

The exciter filters 105 and 106 are filters used at the time of fluorography of an image of the fundus oculi Ef. The exciter filters 105 and 106 can be inserted into and removed from an optical path, respectively, by a drive mechanism like a solenoid or a rotary turret (not shown). The exciter filter 105 is placed on the optical path in the event of FAG (fluorescein angiography). On the other hand, the exciter filter 106 is placed on the optical path in the event of ICG (indocyanine green angiography). At the time of color imaging, both the exciter filters 105 and 106 are retracted from the optical path.

The ring light-transmitting plate 107 is placed in a conjugating location with a pupil of the eye E, and is equipped with a ring light-transmitting part 107a taking an optical axis of the illumination optical system 100 as a center. The mirror 108 reflects the illumination light emitted by the observation light source 101 or by the imaging light source 103, in the direction of the optical axis of the imaging optical system 120. The LCD 109 displays various kinds of images including a fixation target (not illustrated) for fixing the eye E.

The illumination diaphragm 110 is a diaphragm member to shut out part of the illumination light in order to prevent flare, etc. This illumination diaphragm 110 is composed so as to be movable in the direction of the optical axis of the illumination optical system 100, and is thereby capable of adjusting an illumination region of the fundus oculi Ef.

The aperture mirror 112 is an optical element to combine the optical axis of the illumination optical system 100 and the optical axis of the imaging optical system 120. In the center region of the aperture mirror 112, an aperture 112a is opened. The optical axis of the illumination optical system 100 and the optical axis of the imaging optical system 120 cross each other at a substantially central location of this aperture 112a. The objective lens 113 is disposed in the objective lens part 8a of the main body part 8.

The illumination optical system 100 thus configured illuminates the fundus oculi Ef in the following manner. First, at the time of fundus observation, the observation light source 101 is turned on and the observation illumination light is emitted. This observation illumination light is applied to the ring light-transmitting plate 107 via the condenser lenses 102 and 104. (The exciter filters 105 and 106 are retracted from the optical path.) The light passed through the ring light-transmitting part 107a of the ring light-transmitting plate 107 is reflected by the mirror 108, and reflected by the aperture mirror 112 via the LCD 109, the illumination diaphragm 110 and the relay lens 111. The observation illumination light reflected by the aperture mirror 112 advances in the direction of the optical axis of the imaging optical system 120 and is converged by the objective lens 113 to enter the eye E, thereby illuminating the fundus oculi Ef.

At this moment, the ring light-transmitting plate 107 is placed in a conjugating location with the pupil of the eye E and, on the pupil, a ring-shaped image of the observation illumination light entering the eye E is formed. The fundus reflection light of the observation illumination light exits from the eye E through a central dark part of the ring-shaped image on the pupil. Thus, an effect of observation illumination light entering the eye E on the fundus reflection light of the observation illumination light is prevented.

On the other hand, at the time of imaging of the fundus oculi Ef, flush light is emitted from the imaging light source 103 and the imaging illumination light is applied to the fundus oculi Ef through the same path. In the case of fluorography, either the exciter filter 105 or the exciter filter 106 is placed selectively on the optical path, depending on whether FAG imaging or ICG imaging is carried out.

Next, the imaging optical system 120 will be described. The imaging optical system 120 comprises the objective lens 113, the aperture mirror 112 (the aperture 112a thereof), an imaging diaphragm 121, barrier filters 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD 140.

The fundus reflection light of the illumination light exits from the eye E through the central dark part of the ring-shaped image formed on the pupil, and enters the imaging diaphragm 121 through the aperture 112a of the aperture mirror 112. The aperture mirror 112 reflects the cornea reflection light of the illumination light, thereby functioning so as not to mix the cornea reflection light into the fundus reflection light entering the imaging diaphragm 121. As a result, occurrence of flare on the observation images and/or produced images is prevented.

The imaging diaphragm 121 is a plate-shaped member having a plurality of circular light-transmitting parts of different sizes. The plurality of light-transmitting parts compose diaphragms with different diaphragm values (F values), and are placed alternatively on the optical path by a drive mechanism (not illustrated).

The barrier filters 122 and 123 can be inserted into and removed from the optical path, respectively, by a drive mechanism like a solenoid or a rotary turret (not illustrated). In the case of FAG imaging, the barrier filter 122 is placed on the optical path, whereas in the case of ICG imaging, the barrier filter 123 is placed on the optical path. At the time of color imaging, both the barrier filters 122 and 123 are retracted from the optical path.

The variable magnifying lens 124 can be moved in the direction of the optical axis of the imaging optical system 120 by a drive mechanism (not illustrated). This makes it possible to change the magnifying ratio in observation and the magnifying ratio in imaging, and to focus an image of a fundus oculi. The imaging lens 126 is a lens to form an image of the fundus reflection light from the eye E onto the imaging media 9a.

The dichroic mirror 134 reflects the fundus reflection light (having a wavelength in the range of about 400 to 800 nm) of the illumination light. The fundus reflection light of the illumination light reflected by the dichroic mirror 134 enters the half mirror 135 via the field lens 128. Further, (part of) the fundus reflection light passes through the half mirror 135 and enters a dichroic mirror 136 via the relay lens 131.

In addition, the dichroic mirror 134 transmits signal light LS from the OCT unit 150 (for example, having a wavelength in the range of about 800 to 900 nm; described later), and transmits the fundus reflection light of the signal light LS. The signal light LS entering the retinal camera unit 1A from the OCT unit 150 enters the dichroic mirror 134 via a lens 142 and a scanning unit 141. Meanwhile, the fundus reflection light of the signal light LS passed through the dichroic mirror 134 is output from the retinal camera unit 1A via the scanning unit 141 and the lens 142.

The dichroic mirror 136 transmits the illumination light having a wavelength in the visible region from the illumination optical system 100 (visible light having a wavelength of about 400 to 700 nm emitted from the observation light source 101) and reflects the illumination light having a wavelength of the near-infrared region (near-infrared light having a wavelength of about 700 to 800 nm emitted from the imaging light source 103).

Consequently, after passing through the dichroic mirror 136, the fundus reflection light of the observation illumination light is reflected by the reflection mirror 137, and is received by the image pick-up element 12a of the imaging device 12 via the imaging lens 138. Meanwhile, the fundus reflection light of the imaging illumination light is reflected by the dichroic mirror 136, and is received by the image pick-up element 10a of the imaging device 10 via the imaging lens 133.

The image pick-up element 10a of the imaging device 10 is an image pick-up element such as a CCD (charge coupled device) and a CMOS (complementary metal oxide semiconductor), and is particularly used for detecting light having a wavelength of the near-infrared region (that is, the imaging device 10 is an infrared TV camera for detecting near-infrared light).

The imaging device 10 outputs a video signal as a result of detection of near-infrared light. A touch panel monitor 11 displays a two-dimensional image (fundus oculi image Ef') of the surface of the fundus oculi Ef based on the video signal. This video signal is sent to the arithmetic and control unit 200, and the fundus oculi image is displayed on a display (described later).

On the other hand, the image pick-up element 12a of the imaging device 12 is an image pick-up element such as a CCD and a CMOS, and is particularly used for detecting light having a wavelength of the visible region (that is, the imaging device 12 is a TV camera for detecting visible light).

The imaging device 12 outputs a video signal as a result of detection of visible light. The touch panel monitor 11 displays a two-dimensional image (fundus oculi image Ef') of the surface of the fundus oculi Ef based on the video signal. This video signal is sent to the arithmetic and control unit 200, and the fundus oculi image is displayed on the display.

On the LCD 140, a fixation target (internal fixation target) for fixing the eye E, etc. is displayed. After converged by the lens 139, the light emitted from the LCD 140 is reflected by the half mirror 135, and reflected by the dichroic mirror 136 via the field lens 128. Then, the light passes through the imaging lens 126, the relay lens 125, the variable magnifying lens 124, the aperture mirror 112 (aperture 112a thereof), the objective lens 113 and so on, and enters the eye E. As a result, the internal fixation target, etc. is projected on the fundus oculi Ef of the eye E.

The retinal camera unit 1A is provided with the scanning unit 141 and the lens 142. The scanning unit 141 scans an irradiation position on the fundus oculi Ef of the signal light LS entering the retinal camera unit 1A from the OCT unit 150, and functions as one example of the "scanner" according to the present invention.

The lens 142 makes the signal light LS guided from the OCT unit 150 through the connection line 152 enter the scanning unit 141 in the form of a parallel light flux. Further, the lens 142 converges the fundus reflection light of the signal light LS passed through the scanning unit 141, and makes the light enter the connection line 152.

One example of the concrete configuration of the scanning unit 141 is illustrated in FIG. 2. This scanning unit 141 comprises Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by a drive mechanism described later (mirror drive mechanisms 241 and 242 shown in FIG. 5). Consequently, the directions of reflection surfaces (surfaces reflecting the signal light LS) of the Galvano mirrors 141A and 141B, namely, the positions of the Galvano mirrors 141A and 141B are changed, respectively.

The rotary shafts 141a and 141b are arranged perpendicularly to each other. In FIG. 2, the rotary shaft 141a of the Galvano mirror 141A is arranged in parallel to the paper face, while the rotary shaft 141b of the Galvano mirror 141B is arranged perpendicularly to the paper face. In other words, the Galvano mirror 141B is formed so as to be rotatable in the directions indicated by an arrow pointing in both directions in FIG. 2, while the Galvano mirror 141A is formed so as to be rotatable in the directions perpendicular to the arrow pointing in both the directions.

As a result, this pair of Galvano mirrors 141A and 141B act so as to change the reflection direction of the signal light LS to such directions that are perpendicular to each other. As can be seen from FIGS. 1 and 2, the signal light LS is scanned in the x direction when the Galvano mirror 141A is rotated, and the signal light LS is scanned in the y direction when the Galvano mirror 141B is rotated.

The signal lights LS reflected by the Galvano mirrors 141A and 141B are reflected by the reflection mirrors 141C and 141D, thereby advancing in the same directions as when having entered the Galvano mirror 141A.

As described previously, a conductive optical fiber 152a runs inside the connection line 152. The optical fiber 152a is arranged so that an end face 152b thereof faces the lens 142. The signal light LS exiting from the end face 152b advances while gradually expanding its beam diameter toward the lens 142, and is converged to a parallel light flux by the lens 142.

On the contrary, the signal light LS returning from the fundus oculi Ef (fundus reflection light) is converged toward the end face 152b by this lens 142, and guided to the optical fiber 152a.

Configuration of OCT Unit

Next, the configuration of the OCT unit 150 will be described referring to FIG. 3. The OCT unit 150 shown in FIG. 3 is provided with an optical system for forming a tomographic image of a fundus oculi based on data obtained by optical scan (data detected by CCD 184 described below).

The OCT unit 150 has almost the same configuration as a conventional optical image measuring device. That is, the OCT unit 150 comprises: an interferometer that splits the light emitted from a light source into a reference light and a signal light, and generates interference light by superposing the reference light returning from the reference object and the signal light passed from an object to be measured (fundus oculi Ef); and a part configured to detect the interference light and output a signal (detection signal) as a result of the detection to the arithmetic and control unit 200. The arithmetic and control unit 200 forms a tomographic image of the object to be measured (fundus oculi Ef) by analyzing the signal.

A low coherence light source 160 is composed of a broadband light source such as a super luminescent diode (SLD) and a light emitting diode (LED) emitting low coherence light L0. For example, the low coherence light L0 is light having a wavelength of the near-infrared region, and having a timewise coherence length of approximately several tens of micrometers.

The low coherence light L0 emitted from the low coherence light source 160 has a longer wavelength than the illumination light (wavelength of about 400 to 800 nm) of the retinal camera unit 1A, for example, a wavelength within a range of about 800 to 900 nm. The low coherence light source 160 corresponds to one example of the "light source" according to the present invention.

The low coherence light L0 emitted from the low coherence light source 160 is guided to an optical coupler 162 through an optical fiber 161 composed of a single mode fiber or a PM (Polarization maintaining) fiber. The optical coupler 162 splits the low coherence light L0 into reference light LR and signal light LS.

Although the optical coupler 162 has both functions of a part for splitting light (splitter) and a part for superposing lights (coupler), it is conventionally referred to as an "optical coupler".

The reference light LR generated by the optical coupler 162 is guided by an optical fiber 163 composed of a single mode fiber or the like, and emitted from a fiber end face of the fiber. The emitted reference light LR is converged into a parallel light flux by a collimator lens 171, and thereafter, passed through a glass block 172 and a density filter 173 to be reflected by a reference mirror 174 (a reference object).

The reference light LR reflected by the reference mirror 174 passes through the density filter 173 and the glass block 172 again to be converged onto the fiber end face of the optical fiber 163 by the collimator lens 171. The converged reference light LR is guided to the optical coupler 162 through the optical fiber 163.

The glass block 172 and the density filter 173 function as a delaying part for matching the optical path lengths (optical distances) of the reference light LR and the signal light LS, and also functions as a dispersion correction part for matching the dispersion characteristics of the reference light LR and the signal light LS.

The density filter 173 also functions as an ND (neutral density) filter for reducing the amount of the reference light, and is composed of, for example, a rotary ND filter.

The density filter 173 is driven to rotate by a drive mechanism including a drive unit such as a motor (a density filter drive mechanism 244; refer to FIG. 5), thereby functioning so as to change the reduction amount of the reference light LR. Consequently, it is possible to change the amount of the reference light LR contributing to generation of the interference light LC.

The reference mirror 174 is configured to be movable in an advancing direction of the reference light LR (a direction of a solid-line arrow shown in FIG. 3), whereby it is possible to secure the optical path length of the reference light LR according to the axial length of the eye E, etc. The reference mirror 174 is operated to move by a drive mechanism including a drive unit such as a motor (a reference mirror drive mechanism 243; refer to FIG. 5).

On the other hand, the signal light LS generated by the optical coupler 162 passes through an optical fiber 164 composed of a single mode fiber or the like, and enters the connection line 152. The conductive optical fiber 152a runs inside the connection line 152.

The optical fiber 164 and the optical fiber 152a may be composed of a single optical fiber, or may be composed of separate optical fibers formed into one body by connecting end faces thereof. In either case, it is sufficient as long as the optical fibers 164 and 152a are composed so as to be capable of transferring the signal light LS between the retinal camera unit 1A and the OCT unit 150

The signal light LS is led inside the connection line 152 and guided to the retinal camera unit 1A. Then, the signal light LS enters the eye E via the lens 142, the scanning unit 141, the dichroic mirror 134, the imaging lens 126, the relay lens 125, the variable magnifying lens 124, the imaging diaphragm 121, the aperture 112a of the aperture mirror 112, and the objective lens 113 (the barrier filter 122 and 123 are retracted from the optical path in advance when the signal light LS is made to enter the eye E).

The signal light LS having entered the eye E forms an image on the fundus oculi (retina) Ef, and is then reflected. At this moment, the signal light LS not only is reflected on the surface of the fundus oculi Ef, but also reaches the deep area of the fundus oculi Ef to be scattered at the refractive index boundary. As a result, the signal light LS returning from the fundus oculi Ef becomes light containing information reflecting the surface state of the fundus oculi Ef and information reflecting the state of backscatter in the rear at the refractive index boundary of the deep area tissue.

The fundus reflection light of the signal light LS advances reversely on the aforementioned path within the retinal camera unit 1A to be converged onto the end face 152b of the optical fiber 152a, enters the OCT unit 150 through the optical fiber 152a, and returns to the optical coupler 162 through the optical fiber 164.

The optical coupler 162 superimposes the signal light LS returned from the fundus oculi Ef and the reference light LR reflected by the reference mirror 174, thereby generating the interference light LC. The generated interference light LC is led to a spectrometer 180 through an optical fiber 165 composed of a single mode fiber or the like.

The "interference light generator" according to the present invention is composed of an interferometer including at least an optical coupler 162, optical fibers 163 and 164, and a reference mirror 174. Although a Michelson-type interferometer is adopted in the present embodiment, it is possible to adopt any type of interferometer, for example, a Mach Zender type interferometer as necessary.

The spectrometer 180 comprises a collimator lens 181, a diffraction grating 182, an image forming lens 183, and a CCD 184. The diffraction grating 182 used in the present embodiment is a transmission-type diffraction grating that transmits light; however, needless to say, a reflection-type diffraction grating that reflects light may also be used. Further, needless to say, it is also possible to adopt, in place of the CCD 184, other photo-detecting elements. Such a photo-detecting element is one example of the "detector" according to the present invention.

The interference light LC having entered the spectrometer 180 is converged into a parallel light flux by the collimator lens 181, and thereafter, split (resolved into spectra) by the diffraction grating 182. An image of the split interference light LC is formed on the image pick-up surface of the CCD 184 by the image forming lens 183. The CCD 184 receives the interference light LC and converts to an electrical detection signal, and outputs the detection signal to the arithmetic and control unit 200.

Configuration of Arithmetic and Control Unit

Next, the configuration of the arithmetic and control unit 200 will be described. The arithmetic and control unit 200 corresponds to one example of the "computer" according to the present invention.

The arithmetic and control unit 200 analyzes the detection signal input from the CCD 184 of the spectrometer 180 of the OCT unit 150, and performs a process of forming (image data of) a tomographic image of the fundus oculi Ef of the eye E. The analysis method used here is the same analysis method as in the conventional Fourier domain OCT.

Also, the arithmetic and control unit 200 performs a process of forming (image data of) a two-dimensional image showing the state of the surface of the fundus oculi Ef (retina) based on the video signals output from the imaging devices 10 and 12 of the retinal camera unit 1A.

Furthermore, the arithmetic and control unit 200 executes control of the retinal camera unit 1A and the OCT unit 150.

The control of the retinal camera unit 1A is, for example: control of emission of illumination light by the observation light source 101 or the imaging light source 103; control of insertion and retraction operations of the exciter filters 105 and 106 or the barrier filters 122 and 123 to and from the optical path; control of the operation of a display such as the liquid crystal display 140; control of movement of the illumination diaphragm 110 (control of the diaphragm value); control of the diaphragm value of the imaging diaphragm 121; control of movement of the variable magnifying lens 124 (control of the magnification), etc. Further, the arithmetic and control unit 200 performs control of the rotation operation of the Galvano mirrors 141A and 141B within the scanning unit 141 (operation to change the directions of the reflection faces).

Control of the OCT unit 150 is, for example: control of emission of the low coherence light L0 by the low coherence light source 160; control of movement of the reference mirror 174; control of the rotation operation of the density filter 173 (operation to change the reduction amount of the reference light LR); control of the accumulated time of the CCD 184, etc.

One example of the hardware configuration of the arithmetic and control unit 200 acting as described above will be described referring to FIG. 4.

The arithmetic and control unit 200 has a hardware configuration that is the same as conventional computers. To be specific, the arithmetic and control unit 200 comprises: a microprocessor 201 (CPU, MPU, etc.); a RAM202; a ROM203; a hard disk drive (HDD) 204; a keyboard 205; a mouse 206; a display 207; an image forming board 208; and a communication interface (I/F) 209. The respective parts described above are connected via a bus 200a.

Further, the arithmetic and control unit 200 may comprise a reading device such as a card reader for reading recorded content of a patient's card on which patient information including patient identification information such as a patient ID is recorded. This card reader is used, for example, in a state connected to a connector such as a USB (Universal Serial Bus) port (not shown) of a computer forming the arithmetic and control unit 200.

The microprocessor 201 executes operations characteristic to the present embodiment by loading a control program 204a stored in the hard disk drive 204, onto the RAM 202.

Furthermore, the microprocessor 201 executes control of each of the aforementioned parts of the device, various arithmetic processes, etc. Moreover, the microprocessor 201 executes control of each of the parts of the device responding to an operation signal from the keyboard 205 or the mouse 206, control of display processes by the display 207, control of transmitting/receiving processes of various types of data or control signals by the communication interface 209, etc. In addition, the microprocessor 201 has a function of providing date and time information, as usual.

The keyboard 205, the mouse 206 and the display 207 are used as a user interface of the eye movement measuring apparatus 1. The keyboard 205 is used as a device for inputting letters, figures, etc. by typing, for example. The mouse 206 is a pointing device for inputting various kinds of information and performing various operations to a display screen of the display 207.

The display 207 may be any display device composed of an LCD, a CRT (Cathode Ray Tube) or the like. The display 207 displays an image of the fundus oculi Ef formed by the eye movement measuring apparatus 1, and displays a variety of operation screens, set-up screens and so on.

The user interface of the eye movement measuring apparatus 1 is not limited to the above configuration. The user interface can be configured by using any user interface equipped with a function of displaying various information and a function of inputting various information and performing operations, such as a track ball, a control lever, a touch panel type of the LCD, and a control panel for opthalmology examinations.

An image forming board 208 is a dedicated electronic circuit for a process of forming (image data of) an image of the fundus oculi Ef of the eye E. In this image forming board 208, a fundus oculi image forming board 208a and an OCT image forming board 208b are installed.

The fundus oculi image forming board 208a is a dedicated electronic circuit operating to form the image data of the fundus oculi image based on the video signals from the imaging device 10 and the imaging device 12 of the retinal camera unit 1A.

Furthermore, the OCT image forming board 208b is a dedicated electronic circuit operating to form image data of tomographic images of the fundus oculi Ef based on the detection signal from the CCD 184 of the spectrometer 180 in the OCT unit 150.

By mounting such an image forming board 208, it is possible to increase a process speed for forming image data of a fundus oculi image or a tomographic image.

A communication interface 209 operates to send the control signal from the microprocessor 201 to the retinal camera unit 1A and the OCT unit 150. The communication interface 209 also operates to receive the video signals from the imaging devices 10 and 12 of the retinal camera unit 1A and the detection signal from the CCD 184 of the OCT unit 150, and input the signals to the image forming board 208. At this moment, the communication interface 209 operates to input the video signals from the imaging devices 10 and 12 to the fundus oculi image forming board 208a, and input the detection signal from the CCD 184 to the OCT image forming board 208b.

In a case where the arithmetic and control unit 200 is connected to a network such as a LAN (Local Area Network) or the Internet, such a communication interface 209 is used that is equipped with a network adapter such as a LAN card or a communication device such as a modem. In this case, by installing a server accommodating the control program 204a on the network, and at the same time, configuring the arithmetic and control unit 200 as a client terminal of the server, it is possible to cause the eye movement measuring apparatus 1 to execute the operation according to the present invention.

Configuration of Control System of Eye Movement Measuring Apparatus

The configuration of the control system of the eye movement measuring apparatus 1 having the aforementioned configuration will be described referring to FIGS. 5, 6 and 8.

Controller

The control system of the eye movement measuring apparatus 1 is configured centering on a controller 210 of the arithmetic and control unit 200. The controller 210 comprises the microprocessor 201, the RAM 202, the ROM 203, the hard disk drive 204 (control program 204a), and the communication interface 209.

The controller 210 executes the aforementioned control processes in accordance with the control program 204a. In specific, for the retinal camera unit 1A, the controller 210 executes control of the observation light source 101, the imaging light source 103, the Galvano mirrors 141A and 141B (mirror drive mechanisms 241 and 242), etc. For the OCT unit 150, the controller 210 executes control of the low coherence light source 160, the CCD 184, the density filter 173 (density filter drive mechanism 244), the reference mirror 174 (reference mirror drive mechanism 243), etc.

Further, the controller 210 stores an image captured by the eye movement measuring apparatus 1, namely, a two-dimensional image (fundus oculi image Ef) of the surface of the fundus oculi Ef imaged by the retinal camera unit 1A, and a tomographic image of the fundus oculi Ef formed with the detection signal from the OCT unit 150. These images are stored, for example, in the hard disk drive 204. The controller 210 (for example, the hard disk drive 204: an image storage 212 described below; see FIG. 6) functions as one example of the "image storage" according to the present invention.

The image storage of the present invention does not need to be installed in the casing of the arithmetic and control unit 200, and may be a storage device such as an NAS (Network Attached Storage), which is installed outside the casing and to which the arithmetic and control unit 200 can access.

Furthermore, the controller 210 causes the user interface 240 (display 207) to display the images captured by the eye movement measuring apparatus 1. These images may be displayed on the display 207 separately, or may be displayed side by side simultaneously. The detail of the configuration of the controller 210 will be described referring to FIG. 6.

User Interface

The user interface (UI) 240 has a display function configured by a display device such as the display 207, an input function configured by an input device such as the keyboard 205, and an operation function configured by an operation device such as the mouse 206.

Operation Panel

The operation panel 3a is, as shown in FIG. 7, arranged on the mount 3 of the retinal camera unit 1A.

The operation panel 3a is provided with an operation part used for an operation of capturing a two-dimensional image of the surface of the fundus oculi Ef (fundus oculi image Ef') and an operating part used for an operation of capturing a tomographic image of the fundus oculi Ef.

As shown in FIG. 8, the operation panel 3a of the present embodiment is provided with a menu switch 301, a split switch 302, an imaging light amount switch 303, an observation light amount switch 304, a jaw holder switch 305, an imaging switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a predetermined menu screen used by a user to select and designate various types of menus (such as an imaging menu for imaging a two-dimensional image of the surface of the fundus oculi Ef and a tomographic image, a setting menu for inputting various types of settings, etc.).

When the menu switch 301 is operated, a signal of the operation is input to the controller 210. The controller 210 causes the touch panel monitor 11 or the user interface 240 (display 207) to display the menu screen in response to the input of the operation signal. Otherwise, a controller (not shown) may be disposed to the retinal camera unit 1A so that the controller causes the touch panel monitor 11 to display the menu screen.

The split switch 302 is a switch operated to switch turning-on and turning-off of a split bright line for focusing (see JP Patent laid-open No. H9-66031, for example: also referred to as a split target, a split mark and so on.). A configuration for projecting the split bright line onto the eye E (split bright line projection part) is housed, for example, in the retinal camera unit 1A (omitted in FIG. 1).

When the split switch 302 is operated, a signal of the operation is input to the controller 210 (or the aforementioned controller in the retinal camera unit 1A; the same hereinafter). In response to the input of the operation signal, the controller 210 controls the split bright line projection part to project the split bright line onto the eye E.

The imaging light amount switch 303 is a switch operated to adjust the amount of the emission light of the imaging light source 103 (imaging light amount) in accordance with the state of the eye E (for example, the degree of opacity of the lens). The imaging light amount switch 303 is provided with, for example, an imaging light amount increasing switch "+" for increasing the imaging light amount, an imaging light amount decreasing switch "−" for decreasing the imaging light amount, and a reset switch (a button in the middle) for setting the imaging light amount to a predetermined initial value (default value).

When one of the imaging light amount switches 303 is operated, a signal of the operation is input to the controller 210. In response to the operation signal having been input, the controller 210 controls the imaging light source 103 to adjust the imaging light amount.

The observation light amount switch 304 is a switch operated to adjust the amount of the emission light of the observation light source 101 (observation light amount). The observation light amount switch 304 is provided with, for example, an observation light amount increasing switch "+" for increasing the observation light amount, and an observation light amount decreasing switch "−" for decreasing the observation light amount.

When one of the observation light amount switches 304 is operated, a signal of the operation is input to the controller 210. In response to the operation signal having been input, the controller 210 controls the observation light source 101 to adjust the observation light amount.

The jaw holder switch 305 is a switch to move the position of the jaw holder 6 of the retinal camera unit 1A. The jaw holder switch 305 is provided with, for example, an upward movement switch (upward triangle) for moving the jaw holder 6 upward, and a downward movement switch (downward triangle) for moving the jaw holder 6 downward.

When one of the jaw holder switches 305 is operated, a signal of the operation is input to the controller 210. In response to the operation signal having been input, the controller 210 controls a jaw holder movement mechanism (not shown) to move the jaw holder 6 upward or downward. A forehead rest on which the forehead of a subject abuts may be moved together with the jaw holder 6.

The imaging switch 306 is a switch used as a trigger switch for capturing a two-dimensional image of the surface of the fundus oculi Ef or a tomographic image of the fundus oculi Ef.

When the imaging switch 306 is operated in a state where a menu to image a two-dimensional image is selected, the controller 210 receiving a signal of the operation controls the imaging light source 103 to emit imaging illumination light, and also causes the user interface 240 or the touch panel monitor 11 to display a two-dimensional image of the surface of the fundus oculi Ef, based on a video signal output from the imaging device 10 detecting the fundus reflection light.

On the other hand, when the imaging switch 306 is operated in a state where a menu to capture a tomographic image is selected, the controller 210 receiving a signal of the operation controls the low coherence light source 160 to emit the low coherence light L0, controls the Galvano mirrors 141A and 141B to scan the signal light LS, and also causes the user interface 240 or the touch panel monitor 11 to display a tomographic image of the fundus oculi Ef formed by the image forming part 220 (and image processor 230), based on a detection signal output from the CCD 184 detecting the interference light LC.

The zoom switch 307 is a switch operated to change the angle of view (zoom magnification) at the time of imaging of the fundus oculi Ef. Every time the zoom switch 307 is operated, the imaging view angle is alternately set to 45 degrees and 22.5 degrees, for example.

When the zoom switch 307 is operated, the controller 210 receiving a signal of the operation controls a variable magnifying lens driving mechanism (not shown) to move the variable magnifying lens 124 along the direction of the optical axis, thereby changing the imaging view angle.

The image switching switch 308 is a switch operated to switch displayed images. When the image switching switch 308 is operated in a state where a fundus oculi observation image (a two-dimensional image of the surface of the fundus oculi Ef based on the video signal from the imaging device 12) is displayed on the user interface 240 or the touch panel monitor 11, the controller 210 receiving a signal of the operation causes the user interface 240 or the touch panel monitor 11 to display a tomographic image of the fundus oculi Ef.

On the other hand, when the image switching switch 308 is operated in a state where a tomographic image of the fundus oculi is displayed on the user interface 240 or the touch panel monitor 11, the controller 210 receiving a signal of the operation causes the user interface 240 or the touch panel monitor 11 to display a fundus oculi observation image.

The fixation target switching switch 309 is a switch operated to switch a position of the internal fixation target displayed by the LCD 140 (i.e. the projection position of the internal fixation target on the fundus oculi Ef). By operating the fixation target switching switch 309, the position of the displayed internal fixation target can be switched, for example, among "a fixation position to capture an image of the peripheral region of the center of the fundus oculi (fixation position for fundus oculi center imaging)," "a fixation position to capture an image of the peripheral region of macula lutea (fixation position for macula lutea imaging)" and "a fixation position to capture an image of the peripheral region of optic papilla (fixation position for optic papilla imaging)" in a circulative fashion.

In response to the operation signal from the fixation target switching switch 309, the controller 210 causes the LCD 140 to display the internal fixation target in different positions on the display surface. The display positions of the internal fixation target corresponding to the above three fixation positions can be preset based on clinical data, or can be set for each eye E (image of the fundus oculi Ef) in advance.

The fixation target position adjusting switch 310 is a switch operated to adjust the display position of the internal fixation target. The fixation target position adjusting switch 310 is provided with, for example, an upward movement switch for moving the display position of the internal fixation target upward, a downward movement switch for moving it downward, a leftward movement switch for moving it leftward, a rightward movement switch for moving it rightward, and a reset switch for moving it to a predetermined initial position (default position).

Upon reception of the operation signal from one of the switches of the fixation target position adjusting switch 310, the controller 210 controls the LCD 140 to move the display position of the internal fixation target in response to the operation signal.

The fixation target size switching switch 311 is a switch operated to change the size of the internal fixation target. When the fixation target size switching switch 311 is operated, the controller 210 receiving a signal of the operation controls so as to change a display size of the internal fixation target displayed on the LCD 140. The display size of the internal fixation target can be alternately changed, for example, between "a normal size" and "an enlarged size." As a result, the size of a projection image of the fixation target projected onto the fundus oculi Ef is changed. Upon reception of the operation signal from the fixation target size switching switch 311, the controller 210 controls the LCD 140 to change the display size of the internal fixation target in response to the operation signal.

The mode switching knob 312 is a knob rotationally operated to select various types of imaging modes. As selectable imaging modes, it is possible to set any imaging mode such as a fundus oculi imaging mode of imaging a two-dimensional image of the fundus oculi Ef, a B-scan mode of performing B-scan of the signal light LS, and a three-dimensional scan mode of scanning the signal light LS three-dimensionally.

Further, the mode switching knob 312 may be configured so that a replay mode of replaying and displaying a captured two-dimensional image or tomographic image of the fundus oculi Ef can be selected. It may also be configured so that an imaging mode of controlling so as to image the fundus oculi Ef immediately after scanning the signal light LS can be selected. Control of the respective parts of the apparatus in order to cause the eye movement measuring apparatus 1 to execute operations corresponding to the respective modes is executed by the controller 210.

Image Forming Part

The image forming part 220 forms (image data of) a two-dimensional image of the fundus oculi Ef based on video signals from the imaging devices 10 and 12 of the retinal camera unit 1A, and forms (image data of) a tomographic image of the fundus oculi Ef based on a detection signal from the CCD 184 of the OCT unit 150. A tomographic image formation process by the image forming part 220 will be described later. The image forming part 220 comprises the image forming board 208.

The "image forming part" according to the present invention comprises the retinal camera unit 1A, the OCT unit 150, and the image forming part 220. The "tomographic image forming part" according to the present invention comprises the OCT unit 150, and the OCT image forming board 208b of the image forming part 220. The "fundus oculi imaging part" according to the present invention comprises the retinal camera unit 1A, and the fundus oculi image forming board 208a of the image forming part 220.

Image Processor

The image processor 230 executes various kinds of image processing on image data of an image formed by the image forming part 220. For example, the image processor 230 performs a process of forming (image data of) a three-dimensional image of the fundus oculi Ef based on the tomographic image of the fundus oculi Ef according to the detection signal from the OCT unit 150. The image processor 230 also performs various kinds of image correction processes such as brightness correction and dispersion correction of an image.

Here, the image data of a three-dimensional image is image data formed by assigning pixel values to each of a plurality of voxels arranged three-dimensionally, and is referred to as volume data, voxel data or the like. In the case of display of an image based on volume data, the image processor 230 executes a rendering process (such as volume rendering and MIP (Maximum Intensity Projection)) on the volume data to form image data of a pseudo three-dimensional image seen from a particular viewing direction. The controller 210 causes the display 207 to display the pseudo three-dimensional image based on the image data.

Further, as conventional, the image processor 230 executes a process of extracting an image region corresponding to each layer included in a tomographic image of the fundus oculi Ef (for example, pigmented layer of retina) and an image region corresponding to the boundary between the layers, and a process of calculating the thickness of the layer based on the extraction result.

Furthermore, the image processor 230 executes a process of determining the state of eye movement of the eye E based on the two-dimensional image and the tomographic image of the fundus oculi Ef (described below).

The image processor 230 performing the aforementioned processes comprises the microprocessor 201, the RAM 202, the ROM 203, and the hard disk drive 204 (control program 204a).

A mode of scanning the signal light LS for forming a tomographic image of the fundus oculi Ef, and image processing on a tomographic image based on the scanning mode will be described below.

Scanning of Signal Light and Image Processing

The mode of scanning the signal light LS will be described referring to FIGS. 9 and 10. The scanning of the signal light LS is performed by synchronizing control of the operation of the low coherence light source 160 and control of the change of the directions of the reflection surfaces of the Galvano mirrors 141A and 141B of the scanning unit 141. Such synchronous control is realized by control of the low coherence light source 160 and the mirror drive mechanisms 241 and 242 by the controller 210.

When the direction of the reflection surface of the Galvano mirror 141A is changed, an irradiation position of the signal light LS on the fundus oculi Ef is displaced horizontally (in the x direction in FIG. 1). Meanwhile, when the direction of the reflection surface of the Galvano mirror 141B is changed, an irradiation position of the signal light LS on the fundus oculi Ef is displaced vertically (in the y direction in FIG. 1).

When the directions of the reflection surfaces of both the Galvano mirrors 141A and 141B are changed simultaneously, an irradiation position of the signal light LS is displaced in such a direction and by such a distance that the displacement in the x direction and the displacement in the y direction are vectorially composed. In other words, by controlling the Galvano mirrors 141A and 141B, it is possible to scan the signal light LS in any direction and by any distance on the x-y plane.

Figure 9A:
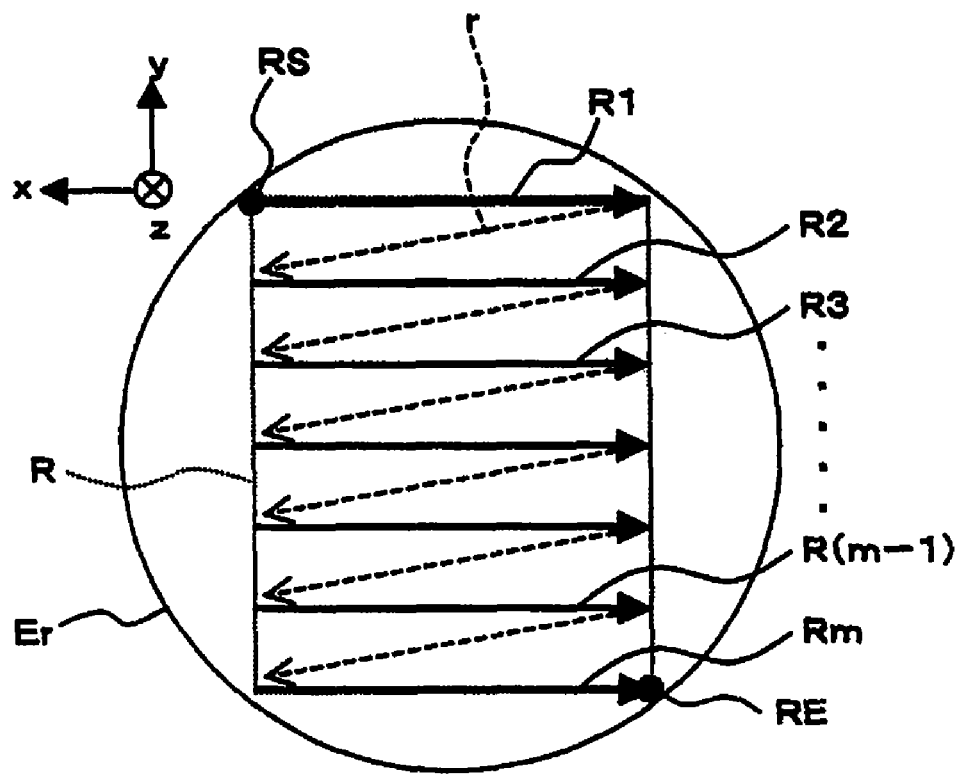
FIG. 9A and FIG. 9B are schematic explanation views for explaining one example of scanning of signal light of the eye movement measuring apparatus according to the preferred embodiment of the present invention.

FIG. 9A shows an example of a mode of scanning the signal light LS when the fundus oculi Ef is seen from a direction that the signal light LS enters the eye E (namely, seen from the −z direction to the +z direction in FIG. 1). Further, FIG. 9B shows an example of a mode of arranging scanning points (positions at which image measurement is carried out; irradiation position of the signal light LS) on each scanning line on the fundus oculi Ef.

As shown in FIG. 9A, the signal light LS is scanned inside a rectangular-shaped scanning region R set in advance. Within the scanning region R, a plurality of (m number of) scanning lines R1 to Rm are set in the x direction. When the signal light LS is scanned along each of the scanning lines Ri (i=1 to m), a detection signal of the interference light LC is generated.

Here, a direction of each of the scanning lines Ri will be referred to as a "main scanning direction" and a direction orthogonal thereto will be referred to as a "sub-scanning direction". Scanning of the signal light LS in the main scanning direction is performed by changing the direction of the reflection surface of the Galvano mirror 141A. Scanning in the sub-scanning direction is performed by changing the direction of the reflection surface of the Galvano mirror 141B.

Figure 9B:
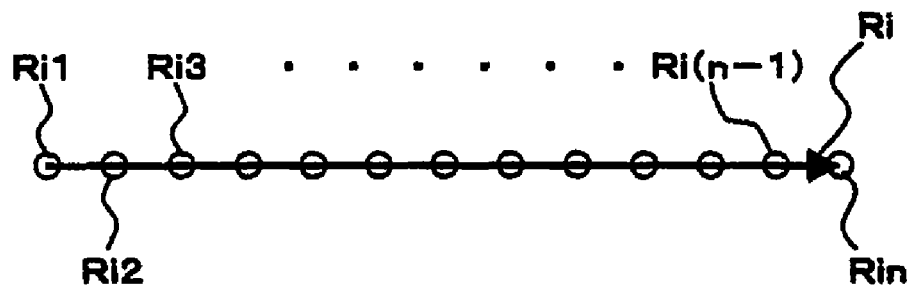

On each of the scanning lines Ri, as shown in FIG. 9B, a plurality of (n number of) scanning points Ri1 to Rin are preset.

In order to execute the scanning shown in FIG. 9, the controller 210 firstly controls the Galvano mirrors 141A and 141B to set the irradiation position of the signal light LS on the fundus oculi Ef to a scan start position RS (scanning point R11) on the first scanning line R1. Subsequently, the controller 210 controls the low coherence light source 160 to flush the low coherence light L0 and make the signal light LS enter the scan start position RS. The CCD 184 receives the interference light LC based on the fundus reflection light of the signal light LS at the scan start position RS, and outputs the detection signal to the controller 210.

Next, the controller 210 controls the Galvano mirror 141A, thereby scanning the signal light LS in the main scanning direction and setting the irradiation position to a scanning point R12. Subsequently, the controller 210 controls so as to flush the low coherence light L0 and make the signal light LS enter the scanning point R12. The CCD 184 receives the interference light LC based on the fundus reflection light of the signal light LS at the scanning point R12, and outputs the detection signal to the controller 210.

Likewise, the controller 210 controls so as to flush the low coherence light L0 at each of the scanning points while moving the irradiation position of the signal light LS to the scanning point R13, R14, - - -, R1(n−1) and R1n in order, thereby obtaining detection signals output from the CCD 184 corresponding to the interference light LC at the respective scanning points.

When the measurement at the last scanning point R1n on the first scanning line R1 is finished, the controller 210 controls the Galvano mirrors 141A and 141B simultaneously to shift the irradiation position of the signal light LS to the first scanning point R21 on the second scanning line R2, following a line switching scan r. Then, by conducting the aforementioned measurement on each of the scanning points R2j (j=1 to n) on the second scanning line R2, the controller 210 obtains detection signals at the respective scanning points R2j.

Likewise, the controller 210 conducts the measurement on the third scanning line R3, - - -, the m−1th scanning line R(m−1) and the mth scanning line Rm, thereby obtaining detection signals at the respective scanning points. Symbol RE on the scanning line Rm is a scan end position corresponding to a scanning point Rmn.

As a result, the controller 210 obtains m×n number of detection signals at m×n number of scanning points Rij (i=1 to m, j=1 to n) within the scanning region R. Hereinafter, a detection signal at the scanning point Rij may be represented by Dij.

When the irradiation position of the signal light LS reaches the last scanning point Rmn, the controller 210 controls the Galvano mirrors 141A and 141B simultaneously to move the irradiation position of the signal light LS along the return scanning line RR shown in FIG. 10. The return scanning line RR corresponds to scanning of the irradiation positions (scanning points) with the signal light LS in the direction from the scan end position RE to the scan start position RS.

Similar to the scanning line Ri of FIG. 9B, a plurality of (n' number of) scanning points RRk (k=1 to n') are previously set on the return scanning line RR. The number (n') of the scanning points RRk on the return scanning line RR may be equal to the number (n) of the scanning points on each of the scanning lines Ri in the main scanning direction, or may be different therefrom. It is desired that an interval between the scanning points on the return scanning line RR (=|RR (k+1)−RRk|; k=1 to n'−1) and an interval between the scanning points on each of the scanning lines Ri (=|Ri(j+1)−Rij|; j=1 to n−1) are equal to each other or set to be nearly equal. The detection signal at the scanning point RRk may be denoted by DRk.

The return scanning line RR is set so as to cross the respective scanning lines Ri (crossing position Ci; see FIG. 11). Assuming there is no displacement of the scanning line Ri caused by movement of the eye E during scanning, a crossing position C1 of the return scanning line RR and the scanning line R1 coincides with the scan start position RS, and a crossing position Cm of the return scanning line RR and the scanning line Rm coincides with the scan end position RE.

An image Gmj shown in FIG. 11 represents an image in the depth direction (z direction) at the scanning point Rmj on the scanning line Rm. When the signal light LS is scanned along the scanning lines R1 to Rm, the image forming part 220 forms depth-wise images Gij based on detection signals Dij at the respective scanning points Rij on the respective scanning lines Ri.

Further, when the signal light LS is scanned along the return scanning line RR, the image forming part 220 forms a depth-wise image (denoted by symbol GRk; not shown) based on a detection signal DRk at each of the scanning points RRk on the return scanning line RR.

Interlocked control of movement of the scanning point of the signal light LS and emission of the low coherence light L0 as described above can be realized by synchronizing, for instance, timing of transmission of control signals to the mirror drive mechanisms 241 and 242 and timing of transmission of a control signal (output request signal) to the low coherence light source 160.

As described above, when controlling the respective Galvano mirrors 141A and 141B to operate as described above, the controller 210 stores the position of each of the scanning lines Ri and the position of each of the scanning points Rij (coordinates on the x-y coordinate system) as information representing the content of the operation. This stored content (scanning point coordinate information) is used in the image formation process as conventional. The scanning point coordinate information is composed of information representing the directions of the reflection surfaces of the Galvano mirrors 141A and 141B, information representing a relative position of the scanning point Rij with reference to any position within the scanning region R (eg., the scan start position RS), and so on.

Next, one example of the processing on an OCT image (tomographic image of the fundus oculi Ef) by the image forming part 220 and the image processor 230 when the mode of scanning the signal light LS shown in FIGS. 9 and 10 is implemented will be described.

The image forming part 220 executes a process of forming a tomographic image of the fundus oculi Ef along each of the scanning lines Ri (in the main scanning direction). The image processor 230 executes a process of forming a three-dimensional image of the fundus oculi Ef based on the tomographic images formed by the image forming part 220.

The process of forming a tomographic image by the image forming part 220, as conventional, includes two steps of arithmetic processes. In the first step of arithmetic process, based on a detection signal Dij at each of the scanning points Rij, the image forming part 220 forms a depth-wise image Gij of the fundus oculi Ef at the scanning point Rij, as described above.

FIG. 11 shows a mode of (a group of) tomographic images formed by the image forming part 220. In the second step of arithmetic process, for each of the scanning lines Ri, the image forming part 220 forms a tomographic image Gi of the fundus oculi Ef along the scanning line Ri, based on depth-wise images Gi1 to Gin at the n number of scanning points Ri1 to Rin on the scanning line Ri. At this moment, the image forming part 220 refers to positional information (the aforementioned scanning point coordinate information) of the scanning points Ri1 to Rin and determines the arrangement and interval of the scanning points Ri1 to Rin, thereby forming the tomographic image Gi along the scanning line Ri.

Through the above process, m number of tomographic images (a group of tomographic images) G1 to Gm at different positions in the sub-scanning direction (y direction) are obtained.

Further, the image forming part 220 forms depth-wise images GR1 to GRn' at the scanning points RR1 to RRn', based on the detection signals DR1 to DRn' obtained by scanning the signal light LS along the return scanning line RR. Furthermore, the image forming part 220 forms a tomographic image along the return scanning line RR (a reference tomographic image GR described later), based on the depth-wise images GR1 to GRn'.

Next, the process of forming a three-dimensional image of the fundus oculi Ef by the image processor 230 will be explained. A three-dimensional image of the fundus oculi Ef is formed based on the m number of tomographic images corresponding to the scanning lines R1 to Rm. The image processor 230 forms a three-dimensional image of the fundus oculi Ef by performing a known interpolating process of interpolating an image between the adjacent tomographic images Gi and G (i+1). However, in a case where the interval between the adjacent tomographic images Gi and G (i+1) is small enough, the interpolating process may be omitted.

Then, the image processor 230 can form a three-dimensional image by referring to the scanning point coordinate information and determining the arrangement and intervals of the scanning lines Ri. For this three-dimensional image, a three-dimensional coordinate system (x, y, z) can be defined based on the positional information (the scanning point coordinate information) of the scanning points Rij and the z coordinates in the depth-wise images.

Further, based on the three-dimensional image, the image processor 230 can form a tomographic image of the fundus oculi Ef at the cross-section in any direction other than the main scanning direction (x direction). When the cross-section is designated, the image processor 230 determines the position of each scanning point on the designated cross-section (and/or an interpolated depth-wise image), extracts a depth-wise image at each determined position (and/or an interpolated depth-wise image) from the three-dimensional image, and arranges a plurality of extracted depth-wise images, thereby forming a tomographic image of the fundus oculi Ef at the designated cross-section.

In a case where eye movement of the eye E occurs during scanning of the signal light LS, the scanning lines R1 to Rm cannot be in the aligned state as shown in FIGS. 9 to 11, and thus displacement of position is caused as shown in FIG. 12. In this case, an actual scanning region R' will be different from the rectangular scanning region R having been set previously.

In a case where eye movement of the eye E occurs during scanning along a given scanning line Ri, displacement is also caused in the scanning point Rij on the scanning line Ri. In the present embodiment, such displacement of scanning points is included in "displacement of a scanning line". In a case where the eye movement occurs during scanning on the scanning line Ri, the scanning line Ri does not become a straight line as shown in FIG. 9 and so on.

In the present embodiment, eye movement of the eye E is measured based on such displacement of a scanning line. The configuration for measurement of eye movement of the eye E based on displacement of a scanning line will be described below.

Detail of Configuration of Arithmetic and Control Unit

The detail of the configuration of the arithmetic and control unit 200 will be described referring to FIG. 6. Here, the controller 210 and the image processor 230 will be detailed.

[Controller]

The main controller 210 of the arithmetic and control unit 200 includes a main controller 211 and an image storage 212.

The main controller 211 executes various control processes of the controller 210 described above.

The image storage 212 stores images formed by the image forming part 220. For example, the image storage 212 stores images such as the tomographic image Gi (i=1 to m) along each scanning line Ri, the reference tomographic image GR along the return scanning line RR, and a fundus oculi image Hp (p=1 to q) which is a two-dimensional image of the surface of the fundus oculi Ef.

Here, the fundus oculi image Hp is an image of each frame composing a moving image captured by video recording of the fundus oculi Ef by using observation illumination light from the observation light source 101. Otherwise, the fundus oculi image Hp may be a series of images imaged by continuously emitting the imaging illumination light (flash light) from the imaging light source 103. Thus, the fundus oculi image Hp is an image obtained by imaging the fundus oculi Ef at predetermined imaging intervals. The imaging intervals of the fundus oculi image Hp may be regular intervals, or may be irregular intervals.

[Image Processor]

The image processor 230 includes an image analysis part 231. This image analysis part 231 analyzes an image of the fundus oculi Ef formed by the image forming part 220 to measure eye movement of the eye E, and functions as one example of the "image analysis part" according to the present invention.

The image analysis part 231 includes a concave-convex detecting part 232 that analyzes the tomographic image Gi of the fundus oculi Ef, and an image region extracting part 233 and a position specifying part 234 that analyze a two-dimensional image of the surface of the fundus oculi Ef.

[Concave-Convex Detecting Part]

The concave-convex detecting part 232 analyzes the tomographic image Gi of the fundus oculi Ef to detect concavities and convexities in an image region corresponding to the layer of the fundus oculi Ef, and functions as one example of the "concave-convex detecting part" according to the present invention. Here, the image region as a detection object of concavities and convexities may be an image region of any layer of the surface and a deep part of the fundus oculi Ef.

The detection of concavities and convexities will be described more specifically. When eye movement of the eye E occurs at the time of capture of the tomographic images G1 to Gm, the aforementioned displacement of scanning lines is caused in these tomographic images G1 to Gm (see FIG. 12).

In specific, if eye movement in the z direction occurs due to pulsation, etc., displacement of scanning lines in the z direction is caused. The z direction is a direction substantially orthogonal to a layer of the fundus oculi Ef, and also a direction in which the depth-wise image Gij of the fundus oculi Ef is formed. Accordingly, the z direction is a cross-sectional direction of the tomographic image Gi.

Further, the image processor 230, as described above, can form a tomographic image along a prescribed direction intersecting the main scanning direction based on a three-dimensional image formed based on the tomographic image Gi. This tomographic image along the prescribed direction is a tomographic image that reflects displacement of a plurality of scanning lines. For example, when a tomographic image having a cross section in the return scanning line RR direction, the tomographic image reflects eye movement occurring while the signal light LS scans each of the scanning lines R1 to Rm.

Figure 13:
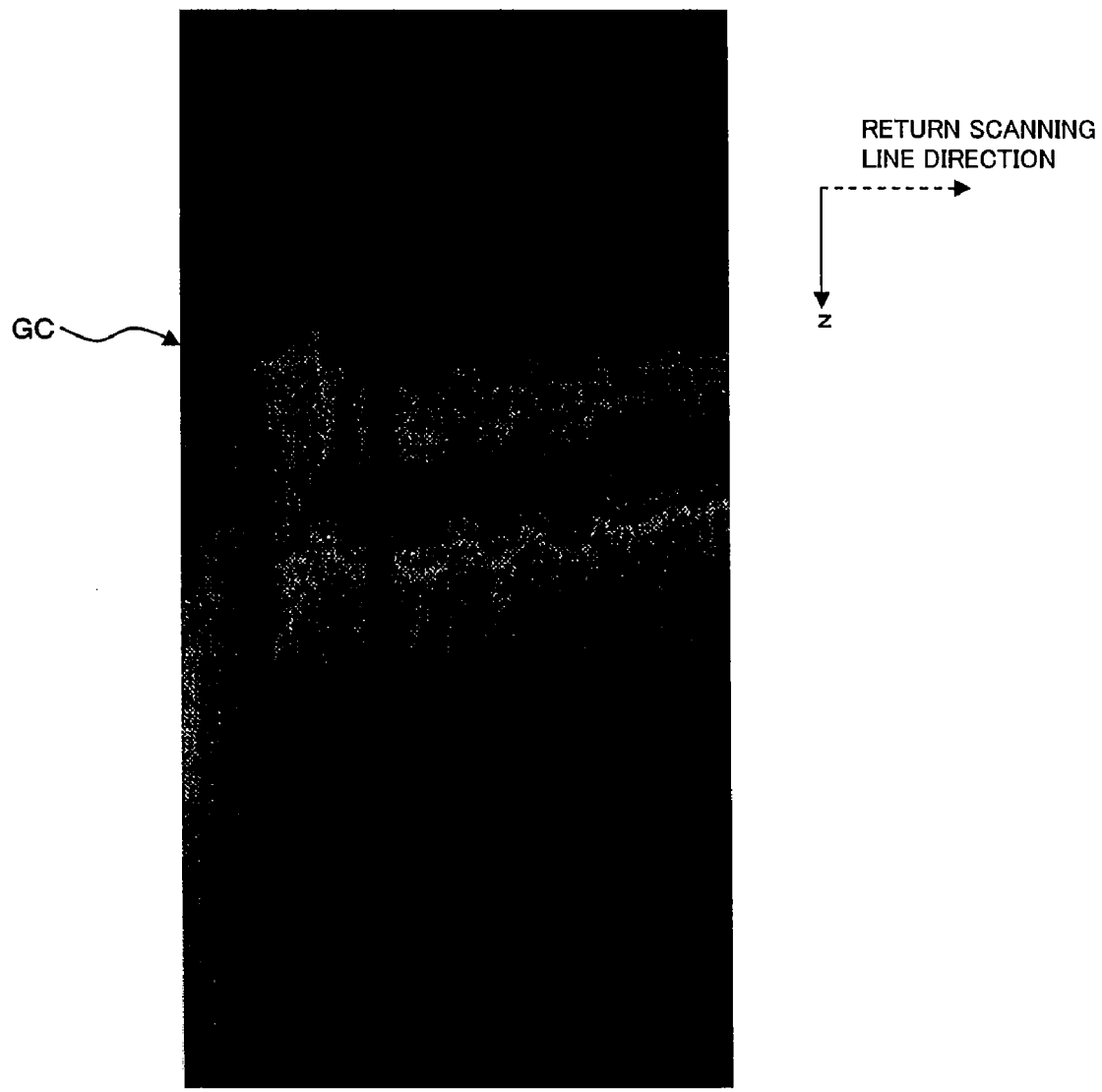
FIG. 13 is a schematic view showing a tomographic image of a fundus oculi formed by the eye movement measuring apparatus according to the preferred embodiment of the present invention.

A tomographic image GC shown in FIG. 13 is a specific example of a tomographic image having a cross section in the return scanning line RR direction. The concave-convex detecting part 232 analyzes the pixel value of the tomographic image GC to extract an image region corresponding to a layer of the fundus oculi Ef. For example, the concave-convex detecting part 232 extracts an image region corresponding to the surface of the fundus oculi Ef by analyzing the pixel value of the tomographic image GC from the −z direction. Consequently, a substantially curved image region having concavities and convexities in the z direction is extracted.

Further, as in the analysis of the tomographic image GC, the concave-convex detecting part 232 extracts an image region corresponding to a layer of the fundus oculi Ef (e.g. the surface of the fundus oculi Ef) on the reference tomographic image GR stored in the image storage 212.

Furthermore, the concave-convex detecting part 232 compares the image region extracted from the tomographic image GC with the image region extracted from the reference tomographic image GR to determine displacement in the z direction of these image regions. A specific example of the process will be described below. First, certain positions (e.g. the scan end positions RE) of these image regions are matched, and the z directions thereof are also matched.

Next, displacement in the z direction between these image regions is determined at each position of the return scanning line RR direction. Consequently, displacement of the image region of the tomographic image GC with respect to the image region of the reference tomographic image GR is obtained.

Another specific example of the process of detecting concavities and convexities by the concave-convex detecting part 232 will be described below. In the specific example described below, an image matching of the tomographic image GC with the reference tomographic image GR is executed, and concavities and convexities of the image region of the tomographic image GC are detected based thereon.

A first concave-convex detecting method using an image matching technique uses a normalized correlation technique. In a case where this technique is used, the concave-convex detecting part 232, while shifting a depth-wise image forming the tomographic image GC by pixel, sequentially calculates a correlation value of normalized correlation between the depth-wise image and a depth-wise image at a corresponding position of the reference tomographic image GR.

Further, the concave-convex detecting part 232 obtains the displacement amount (the number of displaced pixels) $\Delta z_i$ of the depth-wise image when the correlation value becomes the maximum. This displacement amount $\Delta z_i$ is employed as a correction amount in the z direction of the tomographic image Gi along the scanning line Ri corresponding to a position of the depth-wise image (position of the scanning point Rij).

This process is executed for every depth-wise image forming the tomographic image GC. In a case where the tomographic image GC is formed through interpolation, it is sufficient to execute the process only for a depth-wise image at an intersection position between each of the scanning lines Ri and the return scanning line RR.

Instead of the depth-wise image forming the tomographic image GC, the depth-wise image forming the reference tomographic image GR may be shifted. In that case, a displacement amount $\Delta z_i$ with an inverted sign (namely, $-\Delta z$) is employed as the correction amount of the tomographic image Gi. In addition, both the depth-wise image forming the tomographic image GC and the depth-wise image forming the reference tomographic image GR may be displaced.

The amount of displacement in the depth direction (the aforementioned $\Delta z$ and $-\Delta z$) appearing in alignment in the z direction using the normalized correlation technique represents concavities and convexities in the z direction of the tomographic image GC with respect to the reference tomographic image GR. The concave-convex detecting part 232 obtains the displacement amount in the form of the concavities and convexities in the z direction of the tomographic image GC with respect to the reference tomographic image GR.

A second concave-convex detecting method using the image matching technique employs a technique of matching characteristic portions of images. When this technique is used, the concave-convex detecting part 232 extracts the characteristic portion of the depth-wise image forming the tomographic image GC and the characteristic portion of the depth-wise image at the corresponding position in the reference tomographic image GR, respectively.

The characteristic portion to be an extraction object is set previously by the extraction method and the like. Here, a portion corresponding to the surface of the fundus oculi Ef is set as the characteristic portion of the extraction object. One example of the extraction method will be described below.

A case in which the characteristic portion (a part corresponding to the surface of the fundus oculi) of the tomographic image GC shown in FIG. 13 is extracted will be described below. The tomographic image GC is displayed by the user interface 240 (display 207). In the display embodiment, the portion corresponding to the surface of the fundus oculi Ef is displayed on the upper part of the screen and the portion corresponding to a deep portion of the fundus oculi Ef is displayed on the lower part of the screen (see the direction of the z-coordinate in FIG. 13).

Further, the pixel value of a background region of the screen of the display 207 is 0, and the tomographic image GC is displayed as a brightness gray-scale image on the background region (for example, an image composed of 256 tones of brightness (pixel values)).

The concave-convex detecting part 232 refers to the pixel value of each pixel from the upper part to the lower part of the screen for each vertical line of pixels on the display screen of the tomographic image GC. Since the pixel value of the background region is 0, the pixel value keeps 0 for a while during reference of the upper part of the screen. The concave-convex detecting part 232 refers the pixel values further downward to find a pixel where the pixel value is changed from 0 to a positive value.

The coordinate value of the pixel where the pixel value becomes a positive value for the first time is stored in the controller 210 (RAM 202, hard disk drive 204, etc.) as a coordinate value of the part corresponding to the surface of the fundus oculi on the vertical line. As a coordinate system of the coordinate value of the pixel to be stored, the aforementioned x-y-z coordinate system may be used, or a two-dimensional coordinate system set on the screen may be used.

In a case where all the pixel values are 0 down to the lowermost part of the vertical line, it is determined that no image corresponding to the fundus oculi Ef exists on the vertical line.

The concave-convex detecting part 232 executes the same process on each vertical line of pixels on the display screen of the tomographic image GC. Consequently, the part corresponding to the surface of the fundus oculi in the tomographic image GC can be extracted.

Further, the concave-convex detecting part 232 executes the same process on the reference tomographic image GR to extract the part corresponding to the surface of the fundus oculi in the reference tomographic image GR. The process of extraction of the part corresponding to the surface of the fundus oculi herein described is executed in the same manner as extraction of the image region of the surface of the fundus oculi as a layer of the fundus oculi described above.

Furthermore, the concave-convex detecting part 232, while shifting a pixel of the part corresponding to the surface of the fundus oculi of the tomographic image GC by pixel in the z direction, sequentially calculates a correlation value of the pixel of the part corresponding to the surface of the fundus oculi of the reference tomographic image GR (any correlation value can be used appropriately) for each vertical line of the pixel of the display screen.

Then, the amount of displacement of pixels (the number of displaced pixels) when the correlation value becomes the maximum is obtained. The concave-convex detecting part 232 obtains the displacement amount in the form of the concavities and convexities in the z direction of the tomographic image GC with respect to the reference tomographic image GR.

Although the tomographic image GC is shifted in the z direction in the above case, the reference tomographic image GR may be shifted, or both the tomographic images GC and GR may be shifted.

In addition, a characteristic portion other than the part corresponding to the surface of the fundus oculi may be used. For example, in a case where the tomographic image GC and the reference tomographic image GR have a characteristic portion such as a lesioned part, concavities and convexities may be detected by using such characteristic portion.

The concave-convex detecting part 232 can detect not only concavities and convexities in the depth direction (z direction) of the fundus oculi Ef as described above but also the displacement in a direction along the cross section of the tomographic image Gi and the tomographic image GC. For example, displacement in a direction along the scanning line Ri can be detected in the tomographic image Gi. In addition, displacement in a direction along the return scanning line RR can be detected in the tomographic image GC shown in FIG. 13.

[Image Region Extracting Part]

The image region extracting part 233 extracts a noted image region from each of the fundus oculi images Hp (p=1 to q) stored in the image storage 212, and functions as one example of the "image region extracting part" according to the present invention.

Here, the noted image region represents an image region noted when eye movement is measured by using the fundus oculi image Hp. For example, an image region corresponding to any characteristic part in the fundus oculi, such as the optic papilla, macula and a vascular bifurcation of the fundus oculi Ef can be used as the noted image region.

The image region extracting part 233 extracts the noted image region by using a known image extraction technique. For example, in the case of extraction of an image region corresponding to the optic papilla or the macula, the image region extracting part 233 can extract an objective image region by executing, for example, threshold processing on a pixel value of the fundus oculi image Hp.

In addition, in the case of extraction of the vascular bifurcation, the image region extracting part 233 extracts an image region corresponding to a blood vessel among the fundus oculi images Hp first, and then an image region corresponding to a characteristic vascular bifurcation is extracted from the image region corresponding to the blood vessel.

[Position Specifying Part]

The position specifying part 234 specifies a position in the fundus oculi image Hp of the noted image region extracted by the image region extracting part 233 for each of the fundus oculi images Hp, and functions as one example of the "position specifying part" according to the present invention.

The position specifying process will be described more specifically. The two-dimensional coordinate system (x-y coordinate system) corresponding to the x-y-z coordinate system shown in FIG. 1 is set on the fundus oculi image Hp. That is, the position of each pixel forming the fundus oculi image Hp will be specified by the x-y coordinate system. By using that, the position specifying part 234 specifies the position of the noted image region on the fundus oculi image Hp based on the position of a pixel (x-y coordinate value) composing the noted image region extracted by the image region extracting part 233.

Usage of Eye Movement Measuring Apparatus

Usage of the eye movement measuring apparatus 1 according to the present embodiment having the aforementioned configuration will be described below.

Figure 15:
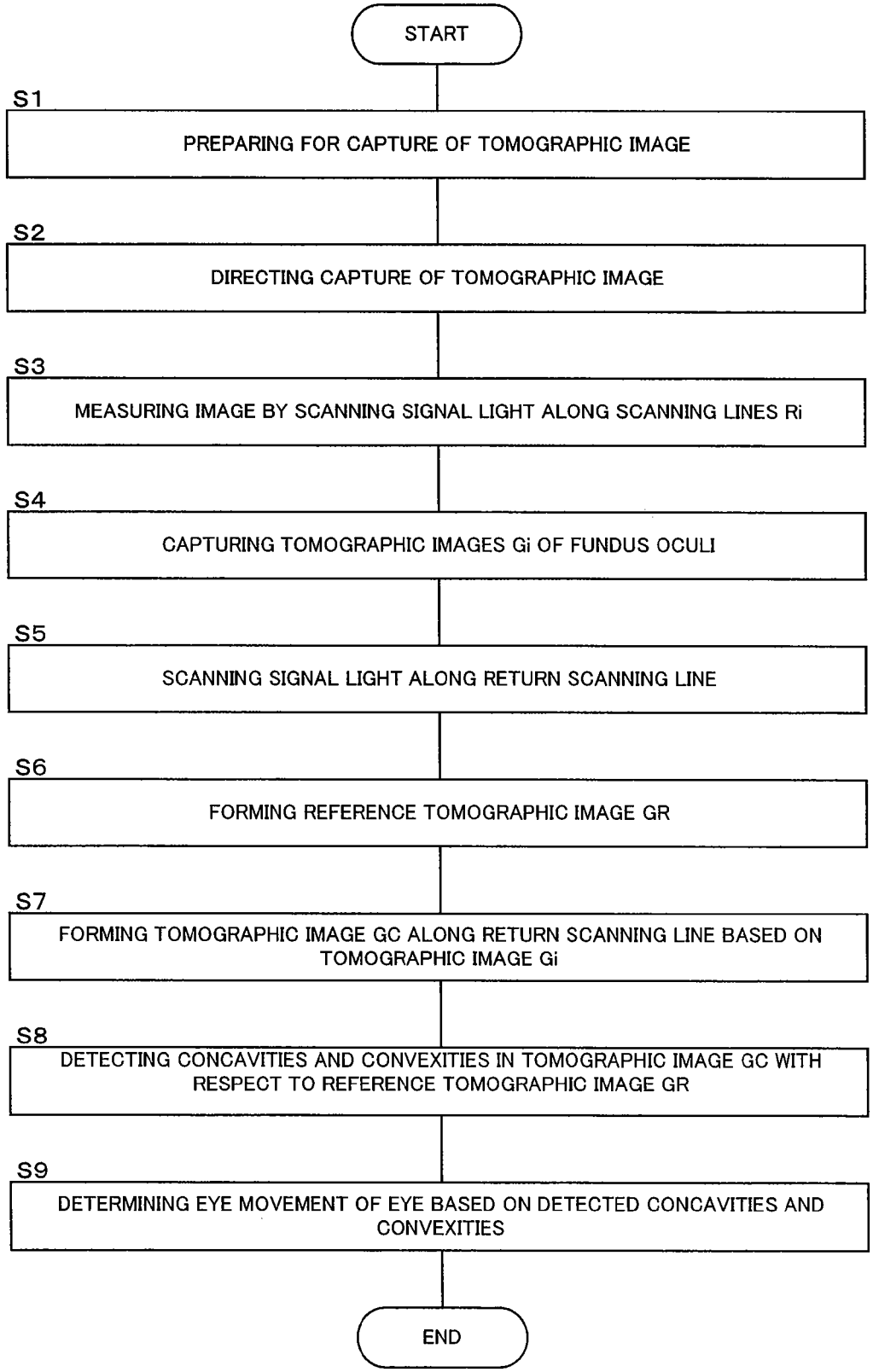
FIG. 15 is a flowchart showing usage of the eye movement measuring apparatus according to the preferred embodiment of the present invention.
Figure 16:
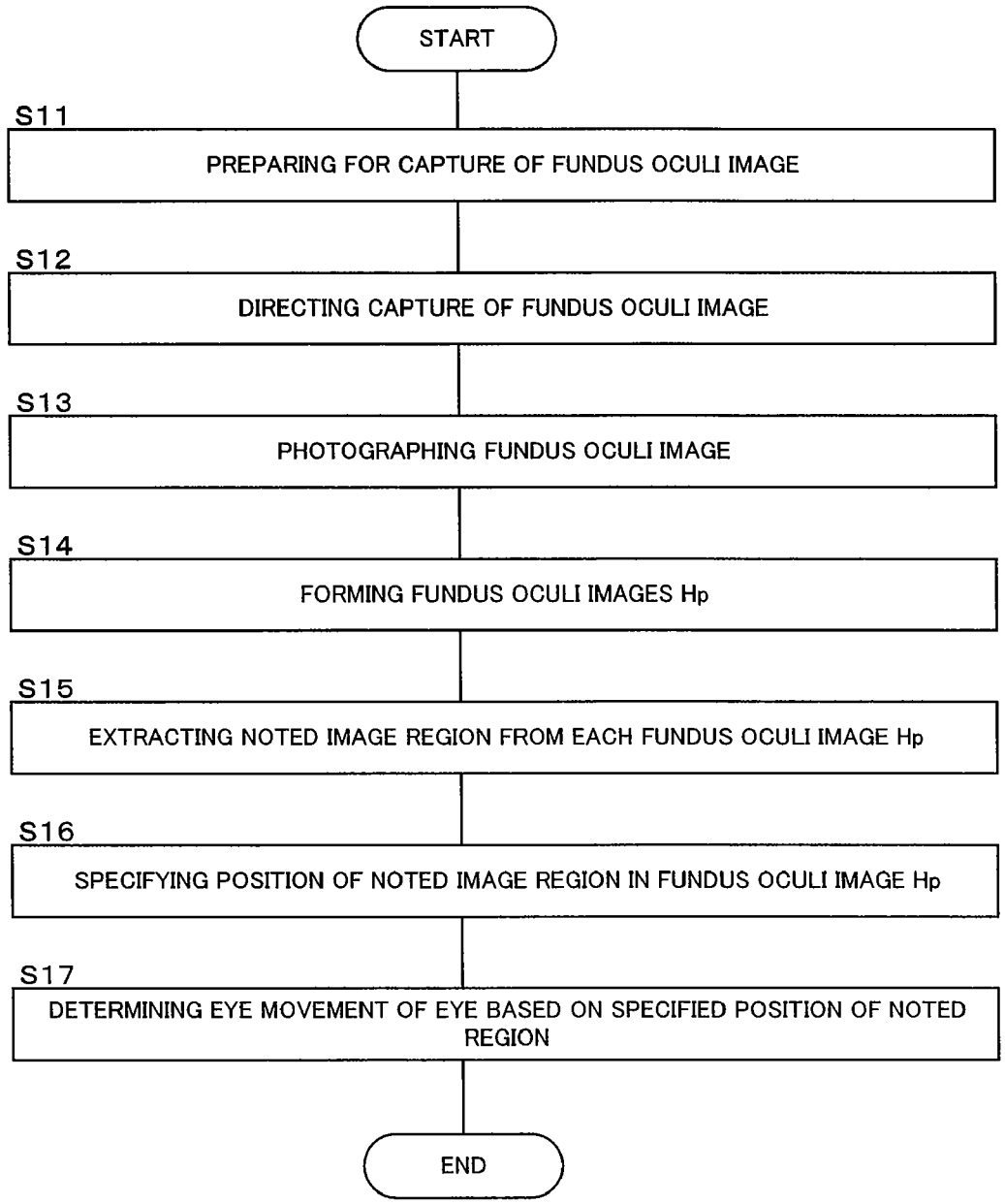
FIG. 16 is a flowchart showing usage of the eye movement measuring apparatus according to the preferred embodiment of the present invention.

Flowcharts shown in FIGS. 15 and 16 represent one example of usage of the eye movement measuring apparatus 1, respectively. Here, the flowchart of FIG. 15 represents one example of measurement of eye movement in the depth direction (z direction) of the fundus oculi Ef. The flowchart of FIG. 16 represents one example of measurement of eye movement in the surface direction (x-y direction) of the fundus oculi Ef.

Measurement of Eye Movement in Depth Direction of Fundus Oculi

Measurement of eye movement of the eye E in the depth direction (z direction) of the fundus oculi Ef will be described referring to the flowchart of FIG. 15.

First, the face of a subject is mounted on the jaw holder 6, and also, various preparations for capturing a tomographic image of the fundus oculi Ef are performed: for example, alignment of the optical system of the retinal camera unit 1A with the eye E, and setting of the apparatus (S1).

When it is ready, the examiner pushes down the operation button 4a to direct capture of a tomographic image (S2). Upon reception of a signal from the operation button 4a, the controller 210 controls the low coherence light source 160, the mirror drive mechanisms 241 and 242, etc., and scans the signal light LS along the scanning lines Ri (i=1 to m), thereby executing image measurement (S3).

The image forming part 220 sequentially forms the tomographic images Gi (i=1 to m) of the fundus oculi Ef based on detection signals from the CCD 184 (S4). The main controller 211 causes the image storage 212 to store the formed tomographic images Gi.

Figure 14:
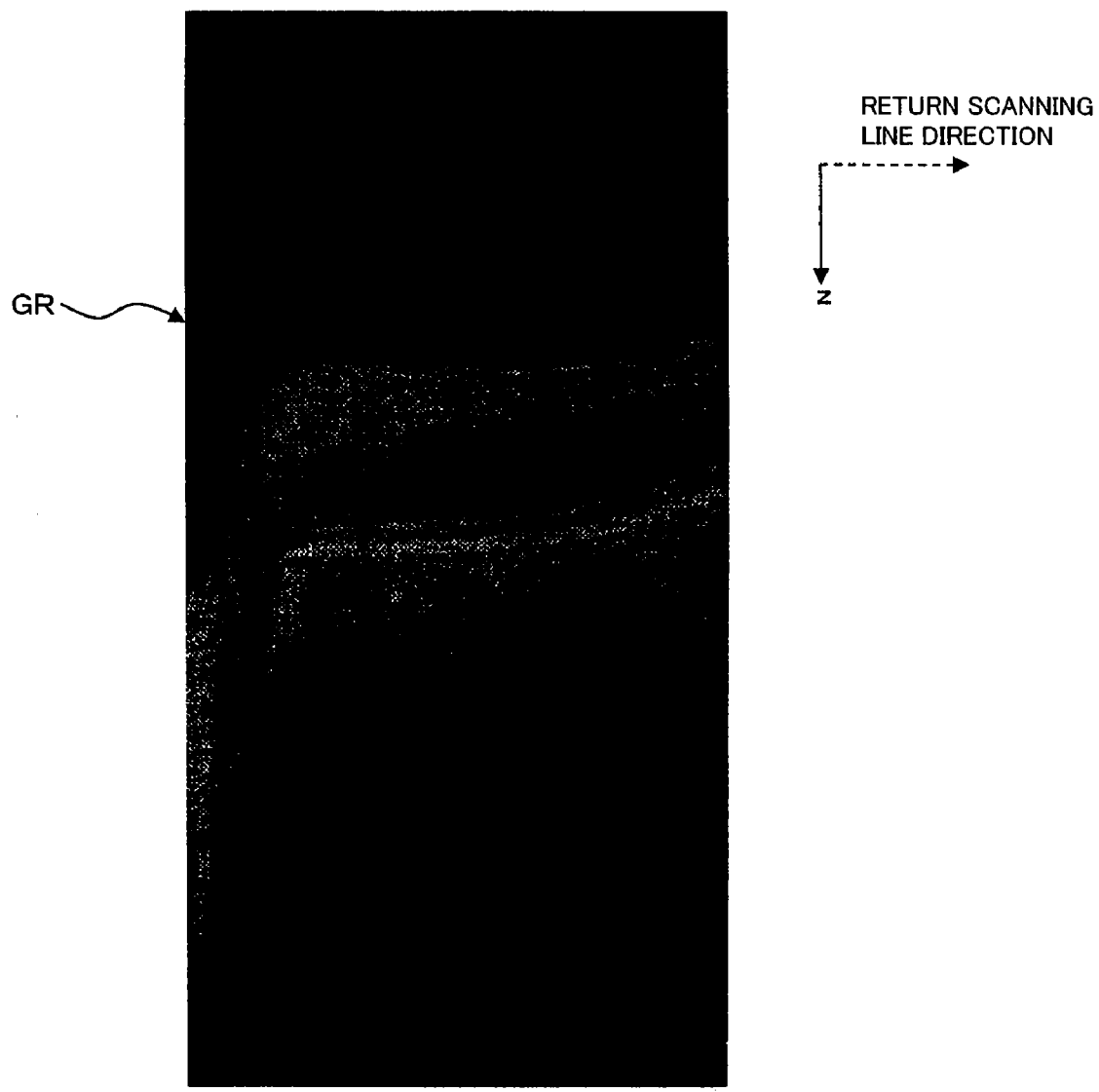
FIG. 14 is a schematic view showing a reference tomographic image of a fundus oculi formed by the eye movement measuring apparatus according to the preferred embodiment of the present invention.

After scanning the signal light LS up to the scanning line Rm, the controller 210 scans the signal light LS along the return scanning line RR (S5). The image forming part 220 forms the reference tomographic image GR (see FIG. 14) based on the detection signal from the CCD 184 (S6). The main controller 211 causes the image storage 212 to store the formed reference tomographic image GR.

The main controller 211 reads out the tomographic images Gi (i=1 to m) and the reference tomographic image GR from the image storage 212, and sends them to the image processor 230. The image processor 230 forms a three-dimensional image of the fundus oculi Ef based on the tomographic images Gi, and further forms the tomographic image GC (see FIG. 13) along the return scanning line RR based on the three-dimensional image (S7).

Next, the concave-convex detecting part 232 detects concavities and convexities in an image region corresponding to a layer of the fundus oculi Ef of the tomographic image GC with respect to the reference tomographic image GR (S8).

The image analysis part 231 determines eye movement of the eye E based on the concavities and convexities of the image region detected by the concave-convex detecting part 232 (S9).

A process at step S9 will be described below. The concavities and convexities detected by the concave-convex detecting part 232 are displacement in the return scanning line RR direction of the tomographic image GC with respect to the reference tomographic image GR. This displacement is represented by $\Delta\zeta$ (=$\Delta z$, $-\Delta z$; described above). Assuming the coordinate value in the return scanning line RR direction is $\alpha$ ($\alpha$ corresponds one-to-one to the coordinate value in x-y coordinate system), the displacement $\Delta\zeta$ can represents $\Delta\zeta=\Delta\zeta(\alpha)$. The image analysis part 231 obtains the displacement $\Delta\zeta(\alpha)$ as displacement in the z direction of eye movement at the coordinate value $\alpha$. The displacement in x-y direction can also be obtained from the detection results by the concave-convex detecting part 232 as described above. This is the end of the description of the measurement of eye movement in the depth direction of the fundus oculi Ef.

According to the present embodiment, the eye movement measuring apparatus is configured to analyze a fundus oculi image of an eye to determine eye movement of the eye. Typically, high accuracy is necessary for capturing a fundus oculi image of an eye. Therefore, compared with measurement of eye movement based on an image imaged by a television camera or a corneal reflection light image as conventional, it is possible to measure eye movement with higher accuracy.

[Modification]

A modification of the measurement of eye movement in the depth direction of the fundus oculi Ef will be described below. Although eye movement in the depth direction of the fundus oculi Ef is simply measured in the above-mentioned usage, it is also possible to measure by extracting a component of the eye movement.

In one example, the concave-convex detecting part 232 can detect concavities and convexities having periodical intervals, based on the tomographic image GC and the reference tomographic image GR. A method for detection is, for example, to obtain a curve approximated to concavities and convexities detected at step S8 (which becomes a wavelike function having a domain in the return scanning line RR direction) to extract frequency component composing the curve by executing frequency analysis. Such frequency component corresponds to concavities and convexities having periodical intervals. The concavities and convexities having periodical intervals detected in this way are equivalent to concavities and convexities caused by factors such as heartbeat occurring periodically.

Measurement of Eye Movement in Surface Direction of Fundus Oculi

Measurement of eye movement of the eye E in the surface direction (x-y direction) of the fundus oculi Ef will be described referring to the flowchart of FIG. 16.

First, the face of a subject is mounted on the jaw holder 6, and also various preparations for capture of fundus oculi images are performed: for example, alignment of the optical system of the retinal camera unit 1A with the eye E and setting of the apparatus (S11).

When it is ready, the examiner pushes down the operation button 4a to direct capture of a fundus oculi image (S12). Upon reception of a signal from the operation button 4a, the controller 210 controls the observation light source 101 (or the imaging light source 103), etc., to image a fundus oculi image (S13).

The image forming part 220 sequentially forms the fundus oculi images Hp (p=1 to q) of the fundus oculi Ef, based on video signals from the imaging device 12 (or the imaging device 10) (S14). The main controller 211 causes the image storage 212 to store the formed fundus oculi images Hp.

The main controller 211 reads out the fundus oculi images Hp (p=1 to q) from the image storage 212, and sends them to the image processor 230. The image region extracting part 233 of the image processor 230 extracts a noted image region from each fundus oculi image Hp (S15).

Next, on each of the fundus oculi images Hp, the position specifying part 234 specifies the position in the fundus oculi image Hp of the noted image region extracted by the image region extracting part 233 (S16).

The image analysis part 231 determines eye movement of the eye E in a direction perpendicular to the depth direction of the fundus oculi Ef (x-y direction; the surface direction of the fundus oculi Ef), based on the position of the noted region specified by the position specifying part 234 on each fundus oculi image Hp (S17).

A process at step S17 will be described below. A position on the fundus oculi image Hp of the noted image region specified by the position specifying part 234 is denoted by (xp, yp). This coordinate value (xp, yp) represents a certain position in the noted image region (for example, the barycentric position). The image analysis part 231 calculates displacement of the position (xp, yp) of the noted image region of the fundus oculi image Hp (p=2 to q) with respect to a position (x1, y1) with reference to a certain fundus oculi image (e.g., a fundus oculi image H1). That is, the image analysis part 231 calculates $\Delta xp=xp-x1$, $\Delta yp=yp-y1$, respectively, for each fundus oculi image Hp (p=2 to q). The calculation results correspond to the displacement of eye movement between when the fundus oculi image Hp is obtained and when the fundus oculi image H1 is obtained. The description of the measurement of eye movement in the surface direction of the fundus oculi Ef is completed.

According to the present embodiment, the eye movement measuring apparatus is configured to analyze a fundus oculi image of an eye to determine eye movement of the eye. Typically, high accuracy is necessary for capturing a fundus oculi image of an eye. Therefore, compared with measurement of eye movement based on an image imaged by a television camera or a corneal reflection light image as conventional, it is possible to measure eye movement with higher accuracy.

Actions and Effects

Actions and effects of the eye movement measuring apparatus 1 according to the present embodiment will be described.

First, the eye movement measuring apparatus 1 operates to optically capture data, form images of the fundus oculi Ef of the eye E (tomographic images, and fundus oculi images) based on the data, and analyze the formed images of the fundus oculi Ef, thereby measuring eye movement of the eye E.

The images of the fundus oculi Ef are more accurate than conventional images for the eye movement measurement, such as images obtained by imaging eye movement with a television camera, corneal reflex light images, etc. Therefore, according to the eye movement measuring apparatus 1 of the present embodiment, it is possible to measure eye movement of the eye E with high accuracy.

Further, according to the eye movement measuring apparatus 1 of the present embodiment, it is possible to measure eye movement of the eye E based on the tomographic image Gi, so that it is possible to highly accurately measure eye movement of the eye E in the depth direction of the fundus oculi Ef having been hard to measure conventionally.

Furthermore, according to the eye movement measuring apparatus 1 of the present embodiment, it is possible to measure eye movement of the eye E based on the fundus oculi image Hp, so that it is possible to highly accurately measure eye movement of the eye E in the surface direction of the fundus oculi Ef.

Eye Movement Measuring Method

The eye movement measuring method according to the present invention comprises an image forming step of capturing data optically to form a fundus oculi image of an eye based on the captured data, and an image analyzing step of analyzing the formed fundus oculi image to measure eye movement of the eye.

The aforementioned eye movement measuring apparatus 1 is one example of a device for preferably implementing the eye movement measuring method. Steps S3 to S7 of the flowchart of FIG. 15 correspond to one example of the image forming step. Steps S8 and S9 correspond to one example of the image analyzing step. In addition, steps S13 and S14 of FIG. 16 correspond to one example of the image forming step. Steps S15 to S17 correspond to one example of the image analyzing step.

Eye Movement Measurement Program

The recording medium causes a computer having an image storage for storing a fundus oculi image of an eye to function as an image analysis part that analyzes the fundus oculi image stored in the image storage and measure eye movement of the eye.

The arithmetic and control unit 200 of the eye movement measuring apparatus 1 described above is one example of a computer that operates in accordance with the recording medium. Here, the image storage corresponds to the image storage 212 shown in FIG. 6. The image analysis part corresponds to the image analysis part 231.

The eye movement measurement program may be recorded on a computer-readable recording medium, such as CD-ROM, CD-R, DVD, DVD-R, USB memory, etc.

Modification

The configuration described above is merely one example to preferably implement of the present invention. Therefore, any modification may be implemented when necessary within the scope of the present invention.

For example, although the eye movement measuring apparatus 1 of the above embodiment is a Fourier domain type OCT device, the configuration of the present invention may be applied to a Time Domain type OCT device. The Time Domain type OCT device is disclosed in Japanese Unexamined Patent Application Publication No. 2005-241464 of the present applicant, for example.

Further, although the eye movement measuring apparatus 1 of the above embodiment is configured to be capable of measuring both eye movement in the depth direction (z direction) of the fundus oculi Ef and eye movement in the surface direction (x-y direction) of the fundus oculi Ef, the eye movement measuring apparatus according to the present invention may be configured to be capable of measuring one of the two measurements.

Furthermore, although the eye movement measuring apparatus 1 in the above embodiment is configured to determine eye movement of the eye E by calculating displacement in the z direction of the tomographic image GC and the reference tomographic image GR, the method for measuring eye movement in the z direction is not limited thereto.

For example, it is possible to determine eye movement, based on only displacement (amplitude) in the z direction of the image region corresponding to a layer of the tomographic image GC (e.g. image region corresponding to the surface of the fundus oculi). However, because it is possible by the method of also employing the reference tomographic image GR to determine displacement of the tomographic image GC by comparing with a reference level which is an image region corresponding to the layer in the reference tomographic image GR, it is considered that measurement of eye movement can be performed with higher accuracy.

In addition, it is also possible to measure the eye movement based on the tomographic image along any direction other than the return scanning line RR.

What is claimed is:

1. An eye movement measuring apparatus comprising:
    an image forming part configured to obtain data optically to form a fundus oculi image of an eye based on the obtained data; and
    an image analysis part configured to analyze the formed fundus oculi image to determine eye movement of the eye,
    wherein the image forming part includes a tomographic image forming part configured to obtain the data by scanning the fundus oculi optically to form a tomographic image of the fundus oculi based on the obtained data,
    wherein the image analysis part determines eye movement of the eye based on the formed tomographic image of the fundus oculi, and
    wherein the tomographic image forming part comprises:
        a light source;
        an interference light generating part configured to generate interference light by splitting light output from the light source into signal light directed toward the fundus oculi of an eye and reference light directed toward a reference object and by overlapping the signal light passed through the fundus oculi and the reference light passed through the reference object;
        a scanning part configured to scan an irradiation position of the signal light on the fundus oculi; and
        a detecting part configured to receive the generated interference light to output a detection signal as the data; and
    the tomographic image forming part forms a tomographic image of the fundus oculi along the scanning direction based on the detection signal corresponding to scanning of the signal light with the scanning part.

2. An eye movement measuring apparatus according to claim 1, wherein the scanning part scans the irradiation position of the signal light on the fundus oculi in a main scanning direction and a sub scanning direction, which are perpendicular to each other, and
    wherein the tomographic image forming part performs the processes of:
        forming a depth-wise image of the fundus oculi at the irradiation position based on the detection signal corresponding to interference light generated from the signal light passed through the irradiation position and the reference light, for each of the plurality of irradiation positions along the main scanning direction;
        forming a tomographic image along the main scanning direction based on the formed depth-wise image at each of the irradiation positions; and thereby forming two or more tomographic images along the main scanning direction at different positions in the sub scanning direction.

3. An eye movement measuring apparatus according to claim 2, wherein the tomographic image forming part forms a tomographic image along a prescribed direction intersecting the main scanning direction based on the two or more formed tomographic images.

4. An eye movement measuring apparatus according to claim 1, wherein the scanning part scans the irradiation position of the signal light at a predetermined time interval, and wherein the image analysis part determines eye movement of the eye based on the tomographic image of the fundus oculi formed by the tomographic image forming part and the predetermined time interval.

5. An eye movement measuring apparatus comprising:

an image forming part configured to obtain data optically to form a fundus oculi image of an eye based on the obtained data; and an image analysis part configured to analyze the formed fundus oculi image to determine eye movement of the eye, wherein the image forming part includes a tomographic image forming part configured to obtain the data by scanning the fundus oculi optically to form a tomographic image of the fundus oculi based on the obtained data, wherein the image analysis part determines eye movement of the eye based on the formed tomographic image of the fundus oculi, and wherein the image analysis part comprises a concave-convex detecting part configured to analyze a tomographic image formed by the tomographic image forming part to detect concavities and convexities of an image region corresponding to a layer of the fundus oculi, and determines eye movement of the eye based on the detected concavities and convexities.

6. An eye movement measuring apparatus according to claim 5, wherein the concave-convex detecting part detects the concavities and convexities in a depth-wise direction of the fundus oculi, and wherein the image analysis part determines eye movement of the eye in the depth-wise direction of the fundus oculi based on the detected concavities and convexities.

7. An eye movement measuring apparatus according to claim 5, wherein the concave-convex detecting part detects the concavities and convexities existing at periodic intervals, and wherein the image analysis part determines eye movement of the eye based on the periodic intervals of the detected concavities and convexities.

* * * * *